United States Patent
Kryger

(12)
(10) Patent No.: US 6,743,448 B2
(45) Date of Patent: Jun. 1, 2004

(54) TOPICAL TESTOSTERONE FORMULATIONS AND ASSOCIATED METHODS

(76) Inventor: Abraham H. Kryger, 1084 Cass St., Suite B, Monterey, CA (US) 93940

(*) Notice: Subject to any disclaimer, the term of this patent is extended or adjusted under 35 U.S.C. 154(b) by 7 days.

(21) Appl. No.: 10/021,564

(22) Filed: Dec. 11, 2001

(65) Prior Publication Data

US 2002/0150625 A1 Oct. 17, 2002

Related U.S. Application Data

(60) Provisional application No. 60/254,713, filed on Dec. 11, 2000.

(51) Int. Cl.[7] ................................................. A61K 9/14
(52) U.S. Cl. ........................ 424/489; 424/484; 424/486; 424/501
(58) Field of Search ................. 424/484, 486, 424/489, 501; 514/772.1

(56) References Cited

U.S. PATENT DOCUMENTS

| | | | | |
|---|---|---|---|---|
| 4,628,052 A | * | 12/1986 | Peat | 514/171 |
| 5,116,606 A | | 5/1992 | Alt | 424/70 |
| 5,152,997 A | * | 10/1992 | Ebert et al. | 424/449 |
| 5,607,691 A | * | 3/1997 | Hale et al. | 424/449 |
| 5,900,242 A | | 5/1999 | Breton et al. | 424/401 |
| 5,935,949 A | * | 8/1999 | White | 514/178 |
| 5,945,409 A | | 8/1999 | Crandall | 514/78 |
| 6,316,428 B1 | | 11/2001 | Crandall | 514/78 |

OTHER PUBLICATIONS

Effects of Transdermal Testosterone Gel on Bone Turnover Markers and Bone Mineral Density in Hypogonadal Men, Wang, C., et al., Clinical Endocrinology (2001) 54, 739–750.

Uptake of Vitamin E Succinate by the Skin, Conversion to Free Vitamin E, and Transport to Internal Organs, Trevithick, J., et al., Biochemistry and Molecular Biology Intnl. (1999) 47, 509–518.

Long–Term Pharmacokinetics of Transdermal Testosteron Gel in Hypogonadal Men, Swerdloff, R., et al., Journal of Clinical Endocrinology & Metabolism, (2000) 85, 4500–4510.

Lecithin Organogel as Matrix for Transdermal Transport of Drugs, Willimann, et al., Journal of Pharmaceutical Sciences, (1992) 81, 871–874.

* cited by examiner

Primary Examiner—Thurman K. Page
Assistant Examiner—Liliana Di Nola-Baron
(74) Attorney, Agent, or Firm—Thorpe North & Western, LLP

(57) ABSTRACT

A topical testosterone formulation is disclosed. In one aspect, the formulation may include a therapeutically effective amount of micronized testosterone, an arginine ingredient, and a tocopherol ingredient admixed with a poloxamer lecithin organogel. Additional ingredients may be included, such as melatonin, oxytocin, DHEA, and progesterone.

22 Claims, 7 Drawing Sheets

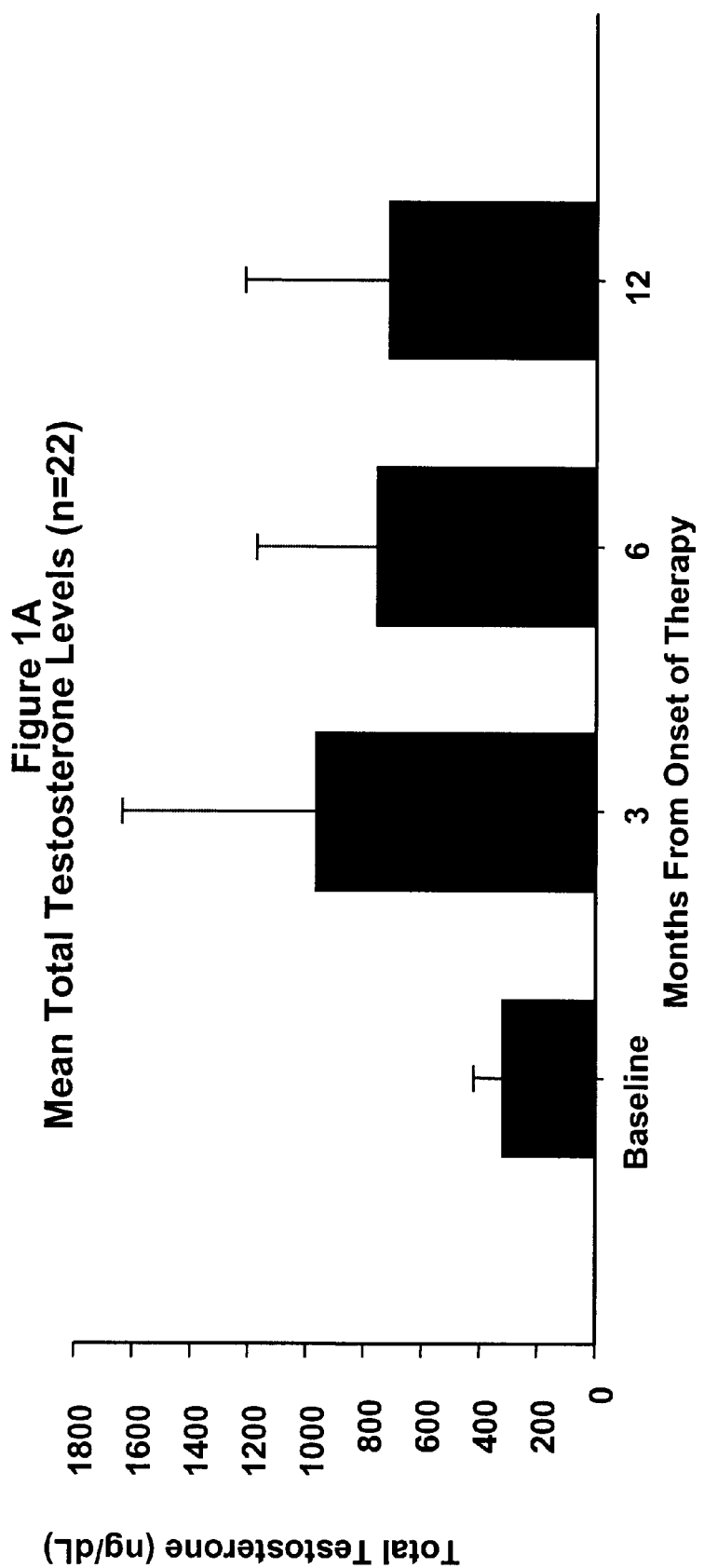

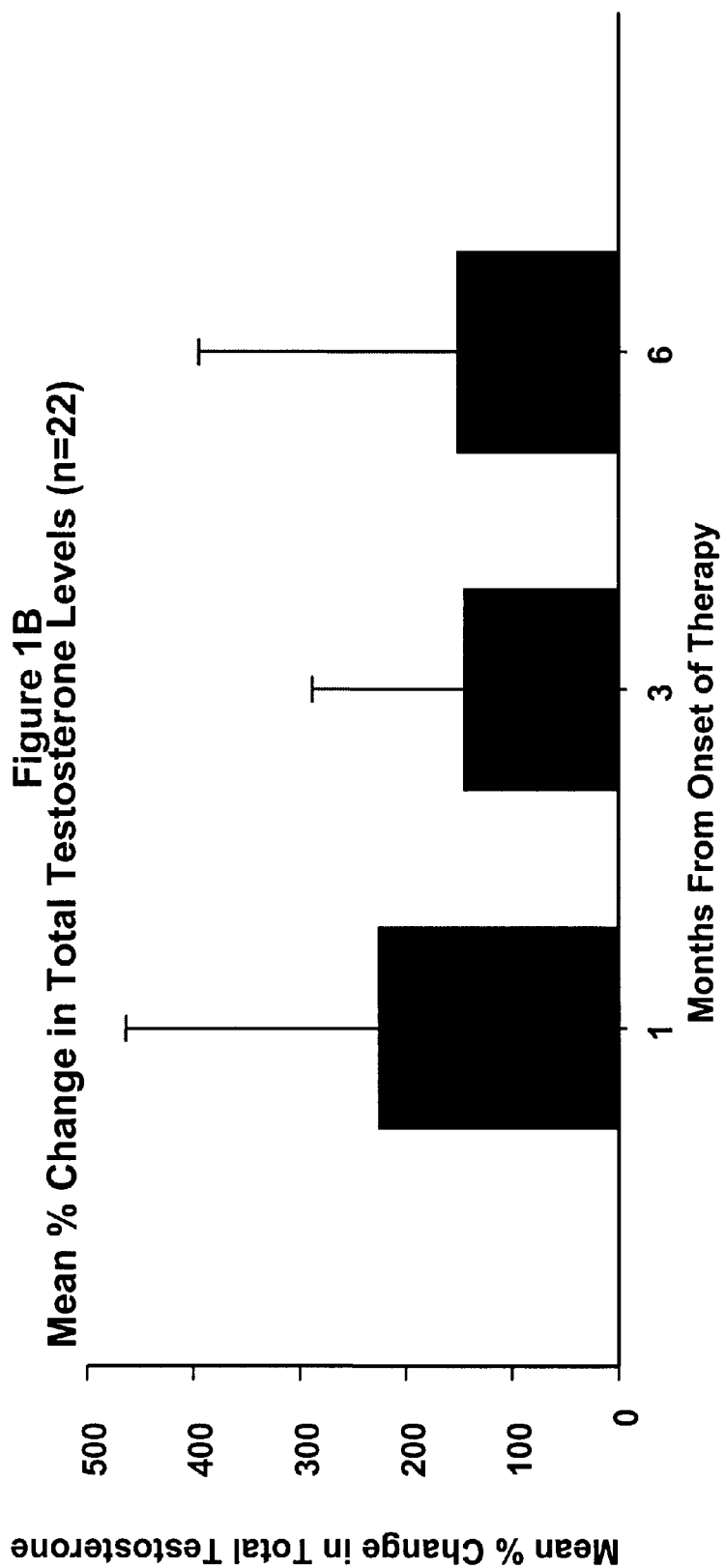

TOPICAL TESTOSTERONE FORMULATIONS AND ASSOCIATED METHODS

PRIORITY INFORMATION

This application claims priority to United States Provisional Patent Application Serial No. 60/254,713, filed on Dec. 11, 2000, which is hereby incorporated by reference.

THE FIELD OF THE INVENTION

The present invention relates to topical testosterone formulations, including methods for making and using such formulations. Accordingly, this invention covers the fields of pharmaceutical sciences and medicine.

BACKGROUND OF THE INVENTION

Hormone replacement therapy has been used in the past to treat patients who have lost the ability to make the hormones or who have reduced hormone levels. Further, testosterone replacement therapy has been used to treat patients with abnormally low testosterone levels.

Numerous diseases currently afflict millions of people world wide that can be partially or wholly treated using testosterone therapy. Examples of such conditions include without limitation: AIDS wasting syndrome, hypogonadism, somatopause, andropause, viropause, other androgen deficiencies in males, anemia, kidney disease, benign prostatic hyperplasia, acne, infertility, constipation, dry eyes, periodontal disease, diabetic retinopathy and other retinopathies, Lupus Erythematosis or other autoimmune diseases, decreased bone density or osteoporosis, heart disease, hyperlipidemias and angina. Further, testosterone replacement therapy has been shown to provide positive health benefits to individuals deficient in testosterone, such as significantly increase muscle strength, mood, cognitive function and energy in men and women, increase insulin-like growth factor in serum and saliva, cause a temporary and reversible decrease in sperm count, and increase the penis size in prepubertal boys and hypogonadal adult men with micropenis.

A number of existing testosterone replacement therapies are known. Unfortunately, most known therapies suffer from one or more disadvantages that reduce treatment efficacy. For example, many known formulations present testosterone in such a manner that much of the dose becomes metabolized into a substantially different product in the plasma, such as estradiol. Further, the manner in which many testosterone formulations are delivered is painful, inconvenient, or provide an inflexible dosage amount, leading to poor patient compliance and subsequent unsuccessful hormone replacement levels.

Examples of specific known testosterone replacement therapies include oral delivery formulations, weekly or bimonthly depot or systemic injections, and topical formulations, such as fixed-dosage transdermal patches or topical gels. Oral administration of many androgens may not be considered a safe or desirable means of replacement because of first-pass hepatic effects, hepatotoxic side effects, and the rare condition of peliosis. Injectable testosterone formulations, including testosterone esters, have issues with pain and self administration, and further may produce toxic liver side effects and significantly fluctuating, hormone levels.

Recently, topical testosterone replacement therapy has been used to replace or increase levels of testosterone for men. Some of these topical applications include fixed dosage patches such as the patches marketed under the name of Testoderm TTS (Alza Pharmaceuticals, Mountain View, Calif.) and Androderm® (Watson Laboratories, Salt Lake City, Utah). Additional transdermal testosterone patches are disclosed in U.S. Pat. Nos. 4,704,282, 5,164,190 and 5,152,997. Further, one example of a low testosterone concentration gel is currently marketed under the name Androgel® (Solvay, Marietta, Ga.).

While fixed-dosage patches have the advantage of mimicking the physiologic production of testosterone through the use of the natural soy-based testosterone USP released in small amounts over 24 hours, the inflexibility in modifying or adjusting dose, may hamper long term treatment efforts. Other drawbacks are also known, such as skin irritation and adhesion problems. Further, the patches are visible on the skin, and while they may be covered with clothing, may be inconvenient or embarrassing when a wearer wishes to engage in various sporting activities which require the removal of clothing, such as swimming, etc.

Testosterone gels, such as the gel recited above, and other hormone replacement gels, such as those disclosed in U.S. Pat. No. 5,855,905, offer the potential for increased convenience to the user as well ease of administration and flexible dosing regimens, as compared to patch testosterone replacement therapies. Unfortunately, such gels also suffer from a number of disadvantages. First, most gels include the active hormones in a low concentration. As a result, the gel must be applied over a substantially large skin surface area in order to achieve therapeutic hormone levels. Such application increases the risk that other individuals in close contact with the patient may inadvertently absorb some of the testosterone. Additionally, much of the testosterone delivered using many known topical formulations, is preferentially aromatized into estradiol (E2), as opposed to being converted to dihydrotestosterone (DHT). Such elevated estrogen levels have been reported to coincide with a increased risk of cancer in many individuals. Other negative physiological effects of testosterone supplementation have been known to occur, such as interference with levels of prostate specific antigen (PSA), and luteinizing hormone.

Therefore, a testosterone replacement formulation which may be administered easily, painlessly, and over a small skin surface area, and which delivers testosterone with minimal estrogen production, or other negative physiological effects, continues to be sought through on-going research efforts.

SUMMARY OF THE INVENTION

Accordingly, the present invention provides a topical testosterone formulation that is capable of providing physiologic testosterone levels when applied to the skin in small amounts, and without significant formation of undesirable estrogen metabolites, such as estradiol. In one aspect, the topical testosterone formulation may include a modified poloxamer lecithin organogel carrier having admixed therein, an arginine ingredient in an amount of from about 0.1 to about 20% w/w, a tocopherol ingredient in an amount of from about 0.1 to about 20% w/w, and a therapeutically effective amount of testosterone. In one aspect, the testosterone may be micronized.

The specific type and amount of testosterone may vary depending on the particular disease or condition being treated, and may be added in any concentration required to achieve a particular result, so long as such concentration does not hinder the testosterone delivery and absorption by the skin. Different formulations may be designed to provide higher or lower testosterone doses. However, in one aspect, the amount of micronized testosterone may be from about 0.5% w/w to about 25% w/w of the formulation. In another aspect, the amount of micronized testosterone is from about 5% w/w to about 10% w/w of the formulation. In yet another aspect, the amount of micronized testosterone may be from about 10% w/w to about 20% w/w of the formulation.

As set forth more fully below, the purpose of the arginine ingredient is to facilitate the production of nitrous oxide (NO) and enhance vasodilation of capillaries. As a fundamental amino acid, arginine may be included in the formulation of the present invention in a variety of forms, including chelated, salt, and derivatized forms, as required in order to achieve a specific result. However, in one aspect, the arginine may be included as a salt form, and in another aspect, the ingredient may be L-arginine monochloride. Further, the arginine ingredient may be from about 5% w/w to about 10% w/w of the formulation.

The tocopherol ingredient is added to the formulation of the present invention as an aromatase inhibitor to help reduce, or minimize, the aromatic conversion of testosterone to an estrogen once the testosterone of the formulation is introduced into the serum. As is known in the art, tocopherol exists in two main forms, alpha tocopherol, and gamma tocopherol. Either form, or a combination of these forms, may be used in the formulation of the present invention. Further, the amount of tocopherol may be from about 5% w/w to about 10% w/w of the formulation.

Additionally, an effective amount of dehydroepiandrosterone (DHEA) may be included in the formulation of the present invention. In one aspect, the DHEA may be the sulfate form, dehydroepiandrosterone sulfate (DHEAS). DHEA administration has been linked to providing a variety of positive health benefits such as improved cognitive function, reduced obesity, etc. While DHEA may be included in the present invention in nearly any concentration required in order to achieve a particularly desired result, in one aspect, the amount of DHEA is from about 1% w/w to about 20% w/w of the formulation. In another aspect, the amount of DHEA may be from about 5% w/w to about 10% w/w of the formulation. Accordingly, in one aspect, the transdermal testosterone formulation may contain from about 50 to about 100 mg of testosterone, from about 10 to about 20 mg of DHEA, from about 1 to about 20 mg of L-arginine and from about 1 to 6 mg of alpha or gamma tocopherol in each 1000 mg of total formulation.

The topical formulation of the present invention may additionally include effective amounts of other ingredients, such as melatonin and oxytocin, which are thought to have various effects on androgenic activity, including the physiology and function of the prostate and other blood chemical interactions. For example, melatonin may be included for its various effects on human prostate epithelium. In one aspect, the amount of melatonin may be from about 1% w/w to about 20% w/w of the formulation. In another aspect, the amount of melatonin may be from about 5% w/w to about 10% w/w of the formulation. Additionally, oxytocin may be included for its capacity in modulating testosterone production, and its ability to monitor the conversion of testosterone to dihydrotestosterone (DHT). In one aspect, the amount of oxytocin may be from about 1% w/w to about 20% w/w of the formulation. In another aspect, the amount of oxytocin may be from about 5% w/w to about 10% w/w of the formulation.

In yet another embodiment of the present invention, progesterone may be included in an effective amount. Specifically, progesterone is thought to have anticancer effects with respect to prostate cancer, as is described in more detail below. Further, the addition of progesterone may be especially applicable when the topical formulation of the present invention is being used to temporarily and reversibly decreasing sperm count (i.e. contraceptive). In one aspect, the amount of progesterone may be from about 1% w/w to about 20% w/w of the formulation. In yet another aspect, the amount of progesterone may be from about 5% w/w to about 10% w/w of the formulation.

The present invention additionally encompasses a method of treating a disease or condition which is responsive to testosterone therapy. In general, such a method includes the step of administering a topical testosterone formulation as disclosed herein to the skin of a subject. A wide variety of diseases or conditions may be responsive to testosterone therapy, including without limitation: AIDS Wasting Syndrome, micropenis, somatopause, andropause, viropause, or androgen deficiency in adult males (ADAM), anemia from renal dialysis or chronic kidney disease, benign prostatic hyperplasia, acne, diabetes, infertility, periodontal disease, post anabolic steroid abuse, dry eyes, diabetic retinopathy, retinopathy, and Lupus Erythematosis decreased bone density (i.e. osteoporosis), hyperlipemia, predisposition toward prostrate cancer, heart disease, angina, and hypertension. Further, other symptoms resulting from testosterone deficiency may include without limitation, infrequent early morning erections, small penis size in prepubertal boys, subphysiologic levels of insulin-like growth factor (IGF-1, poor muscle strength, poor cognitive function, poor mood, and low energy. It is recognized that one or more of such symptoms may be the result of a naturally occurring disease or condition, or one that is brought on by habits or activities of the subject, such as opioid or steroid abuse.

A variety of routines and regimens may be used in order to effect treatment of the diseases or conditions recited above, and each specific situation may merit a customized dosage and duration, which can be readily determined by a physician, or other individual of ordinary skill in the art. However, in one aspect, the formulation may have a testosterone content of about 10% w/w, and be administered in an amount of from about 0.5 g to about 2 g once a day on a daily basis routine for at least about 30 days. Such a regime may achieve a serum testosterone level of from about 600 ng/dl to about 1200 ng/dl. Further, while the topical formulation may be applied to any location on the skin or mucosa, in one aspect, the formulation is administered to hairless skin along the rib area below the armpit and the underarm and/or to the scrotal skin.

As is known by those of ordinary skill in the art, testosterone levels may be measured in a variety of ways, including in the blood serum, and in saliva. One method for measuring the efficacy of hormone treatment is by measuring the levels achieved with the supplementation and comparing the level attained to levels considered to be within a normal range. The serum or saliva levels obtained at a give time interval, including peak serum levels, depend on a variety of factors, including the amount of hormone administered and the permeation rate at which the hormone permeates through the skin, and the rate at which the hormone is cleared from the skin and into the blood serum. However, in one aspect, the administration of the topical testosterone formulation of the present invention results in peak levels of serum or salivary testosterone within about 24 to about 36 hours after application. In another aspect, the administration may result in sufficiently high salivary levels of free testosterone and dihydrotestosterone to prevent the conversion of excess testosterone to estradiol.

The present invention also encompasses a method of minimizing aromatic conversion of testosterone to an estrogen during testosterone supplementation therapy. Such a method includes the steps of providing a topical testosterone formulation comprising a poloxamer lecithin organogel having admixed therein, an arginine ingredient in an amount of from about 0.1 to about 20% w/w, and a tocopherol ingredient in an amount of from about 0.1 to about 20% w/w, and a therapeutically effective amount of micronized testosterone, and administering the formulation to the skin of a subject. As recited above, the tocopherol is an aromatase inhibitor which aids in suppressing the aromatic metabolization of testosterone into an estrogen. As such, a greater portion of the testosterone which becomes metabolized is metabolized into dihydrotestosterone (DHT), and further free testosterone levels are increased. In some aspects, it is thought that the higher concentrations of free testosterone and DHT may further work to suppress the conversion of testosterone into estrogen.

BRIEF DESCRIPTION OF THE DRAWINGS

FIGS. 1A–B show the mean percentage change from baseline in total testosterone levels (ng/dl) in 22 men at 3, 6, and 12 months, and 1, 3, and 6 months respectively, after initiation of daily administration of a topical testosterone formulation containing about 10% w/w testosterone in accordance with one aspect of the present invention.

DETAILED DESCRIPTION

A. Definitions

Figure 2:
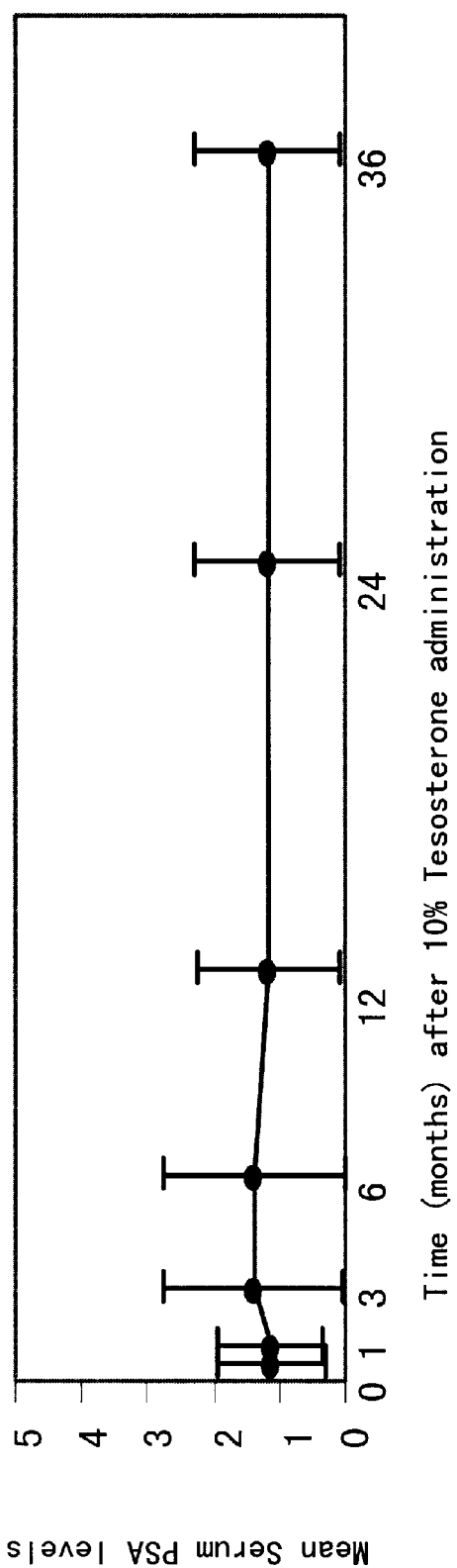
FIG. 2 shows the mean serum PSA levels (ng/ml) of 22 subjects (ages 22–81 years old) measured 30, 90, 180, 360, 720, and 1080 days after administration of daily doses (0.5 cc–2.0 cc) of a topical testosterone formulation containing about 10% w/w testosterone in accordance with one aspect of the present invention. The normal PSA range in men (0.0–0.4 ng/ml) is indicated by the dashed lines.

In describing and claiming the present invention, the following terminology will be used.

The singular forms "a," "an," and "the" include plural referents unless the context clearly dictates otherwise. Thus, for example, reference to "a hormone" includes reference to one or more of hormones, and reference to "an enhancer" includes reference to one or more of such enhancers.

As used herein, "testosterone" refers to the compound having the IUPAC names (17)-17-Hydroxyandrost-4-en-3-one, and $\Delta^4$-androsten-17-ol-3-one, as well as their isomers. Testosterone is listed in the Merck Index, entry no. 9322, at page 1569, 12th ed., (1996), which is incorporated herein by reference. Testosterone may be obtained or prepared using the knowledge of one ordinarily skilled in the art from either a natural source, or synthetically using a process, such as those disclosed in U.S. Pat. No. 2,236,574 which is incorporated herein by reference. Further, a number of closely related androgenic compounds which are synthetically derivatized from testosterone are known to provide the same or a similar physiologic activity. Such compounds include without limitation, testosterone salts, such as acetate, enanthate, cypionate, isobutyrate, propionate, and undecanoate esters, cyproterone acetate, danazol, finasteride, fluoxymesterone, methyltestosterone, nandrolone decanoate, nandrolone phenpropionate, oxandrolone, oxymetholone, stanozolol, and testolactone. However, as used herein, "natural," or "native" testosterone, refers to (17)-17-Hydroxyandrost-4-en-3-one, or $\Delta^4$-androsten-17-ol-3-one.

As use herein, "estrogen" refers to any substance, natural or synthetic, that exerts a biological or pharmacological action primarily by binding to estrogen receptors. Examples include but are not limited to: estradiol, such as 17-β-estradiol, 17-α-estradiol, estriol, estrone, and phytoestrogens.

As used herein, "administration," and "administering" may be used interchangeably, and refer to the act of presenting, applying, or introducing a drug to a subject in order to achieve a desired physiological or psychological response.

As used herein, "topical formulation" refers to a composition including a carrier, in which the drug may be placed for direct application to a skin surface and from which an effective amount of drug is released. Examples of topical formulations include but are not limited to ointments, creams, gels, and pastes.

As used herein, "carrier," and "pharmaceutically acceptable carrier" may be used interchangeably, and refer to any liquid, gel, salve, solvent, liquid, diluent, fluid ointment base, liposome, micelle, giant micelle, and the like, which is suitable for use in contact with living animal or human tissue without causing adverse physiological responses, and which does not interact with the other components of the composition in a deleterious manner. A number of carrier ingredients are known for use in making topical formulations, such as gelatin, polymers, fats and oils, lecithin, collagens, alcohols, water, etc. One specific carrier which has been found to be particularly useful in the topical formulation of the present invention is a poloxamer lecithin organogel carrier.

As used herein, "poloxamer lecithin organogel," and "pluronic lecithin organogel," (PLO) may be used interchangeably, and refer to a pharmaceutically acceptable carrier that includes one or more poloxamer compounds, and a lecithin component, in addition to other ingredients such as water. PLO's are well known to those skilled in the art, and may utilize a number of specific poloxamer compounds. Poloxamer compounds are well known to those skilled in the art as a family of polymers that contain polypropylene oxide, (PPO) and polyethylene oxide (PEO) segments in the sequence PEO-PPO-PEO Further, "pluronic" refers to poloxamer compounds that are sold collectively under the trademark PLURONIC (BASF, Parsippany, N.J.). In one aspect, PLURONIC F-127 (PL 127) corresponds to poloxamer 407, a polyoxypropylene-polyoxyethylene block copolymer described by Schmolka in the *Journal of Biomedical Materials Research* 6:571–582, 1972.

As used herein, "modified poloxamer lecithin organogel," or "modified pluronic lecithin organogel" (MPLO) refers to an organogel having a modified or high ratio of poloxamer to lecithin content. The formation of such gels is also known in the art, and may be accomplished by reducing the amount of water in a PLO formulation. In one aspect, the amount of poloxamer may be about 20% w/w or greater. Further, the poloxamer amount may be 30% w/w or greater.

As used herein, "admixed" means that the drug and other ingredients can be dissolved, dispersed, or otherwise suspended in the carrier.

As used herein, with respect to testosterone, "micronized" refers to a particle size which is less than about 100 micrometers.

As used herein, "disease," and "condition" may be used interchangeably, and refer to one or more physical or psychological signs, symptoms, or laboratory findings, which indicate an illness, deficiency, or other abnormal state of well being.

The terms "formulation" and "composition" are used interchangeably herein. The terms "pharmaceutical" and "drug" are also used interchangeably to refer to a pharmacologically active substance or composition. These terms of art are well-known in the pharmaceutical and medicinal arts.

As used herein with reference to biological or serum amounts of a substance, "physiologic level" refers to a level considered to be normal in a healthy individual. As such, "superphysiologic level" would be a level considered to be higher than normal, and "subphysiologic level" would be a level considered to be lower than normal, or indicate a deficiency.

As used herein, "free testosterone," "unbound testosterone," or similar terms, refers to testosterone which is unattached to any protein, such as SHBG, or albumin. Serum free testosterone levels can be measured by a variety of laboratory methods known to those skilled in the art, including equilibrium dialysis, ultra filtration, an analogue RIA method, and by calculation from the levels of total testosterone, SHBG and albumin. See, for example, Winters et al. *The Analog Free Testosterone Assay: Are the Results in Men Clinically Useful?, Clinical Chemistry* Vol. 44:2178–2182 (1998); see also, Vermeulen et al. (1999). The equilibrium dialysis method, is currently believed to provide the most accurate results. See, Mathor et al., *Free Plasma Testosterone Levels During the Normal Menstrual Cycle, J. Endocrinol Invest* Vol. 8:437–41 (1985).

As used herein, "bioavailable testosterone" and similar terms refer to testosterone that is not bound to SHBG. Therefore testosterone which is "free" (unbound) or "weakly bound to" (easily dissociates from) serum albumin is considered to be bioavailable to tissues. Because of the high binding capacity (non-saturability) of albumin for testosterone, the serum concentration of albumin-bound testosterone will, in general, be proportional to the concentration of free testosterone. The proportionality factor corresponds to the product of the albumin-testosterone binding constant ($3.6 \times 10^4$ L/mole) and the serum albumin concentration (expressed in mole/Liter). See, Vermeulen et al., *A Critical Evaluation of Simple Methods for the Estimation of Free Testosterone in Serum, J. of Clinical Endocrinology and Metabolism* Vol. 84:3666–3672 (1999). The concentration of bioavailable testosterone is commonly measured using an ammonium sulfate precipitation method. See, for example, Nankin et al. *Daytime Titers of Testosterone, LH, Estrone, Estradiol, and Testosterone-Binding Protein: Acute Effects of LH and LH-Releasing Hormone in Men, J. Clinical Endocrinology Metabolism,* Vol. 41:271–81 (1975).

As used herein, "total testosterone" refers to the sum of: (1) free testosterone; (2) testosterone which is weakly bound to serum proteins, such as albumin-bound testosterone; and (3) testosterone which is tightly bound to high affinity binding serum proteins, such as SHBG-bound testosterone. Total serum testosterone can be measured by known assay techniques such as a radioimmunoassay (RIA). See for example the RIA procedure used by Endocrine Sciences, Inc. (Calabassas Hills, Calif.). This procedure is based on the published RIA by Furuyama et al., *Radioimmunoassay for Plasma Testosterone, Steroids.* 1970;16:415–428.

As used herein, "skin," "skin surface," "derma," "epidermis," and similar terms are used interchangeably herein, and refer to not only the outer skin of a subject comprising the epidermis, but also to mucosal surfaces to which a drug composition may be administered. Examples of mucosal surfaces include the mucosal of the respiratory (including nasal and pulmonary), oral (mouth and buccal), vaginal, introital, labial, and rectal surfaces. Hence the terms "transdermal" encompasses "transmucosal" as well.

As used herein, "effective amount" refers to an amount of a substance which is sufficient to achieve its intended purpose or effect. Various biological factors may affect the ability of a delivered substance to perform its intended task. Therefore, an "effective amount" may be dependent on such biological factors. Further, determination of the effectiveness of the amount is well within the knowledge and ability of one of ordinary skill in the art.

As used herein, a "therapeutically effective amount" refers to an amount of a substance which is capable of achieving a desired physiologic or psychologic result to a selected degree. While the achievement of therapeutic effects may be measured by a physician or other qualified medical personnel using evaluations known in the art, for example with testosterone supplementation therapy, physical examination, blood and saliva tests may be used, it is recognized that individual variation and response to treatments may make the achievement of therapeutic effects a subjective decision.

As used herein, "hyperlipemia" refers to an excessive quantity of fat in the blood. Further, "hyperlipidemia" refers to an increase of lipids in the blood. Specific symptoms of such conditions include without limitation, super physiologic or elevated triglyceride levels, and low density lipid (LDL) cholesterol levels.

As used herein with respect to a disease or condition, "predisposition" and "genetic predisposition" may be used interchangeably, and refer to a greater than normal likelihood that a specific disease or condition will occur in an individual due to a family history thereof.

As used herein, "percent by weight" and "%w/w" refer to the amount of an indicated component with respect to an entire composition of which the component is a part. By way of example, tocopherol in an amount of 20% w/w refers to the amount of tocopherol being 20% of the weight of the total formulation which contains the tocopherol.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a concentration range of 0.01% w/w to 20% w/w should be interpreted to include not only the explicitly recited concentration limits of 0.1% w/w and 20% w/w but also to include individual concentrations within that range, such as 0.5% w/w, 1.0% w/w, 5% w/w, 10% w/w, 15% w/w, and sub-ranges such as 0.5–5% w/w 5–10% w/w, 10–15% w/w, etc. This interpretation applies to open-ended ranges reciting only one numerical value as well, such as "less than about 20% w/w," and should apply regardless of the breadth of the range or the characteristic being described.

B. The Invention

The present invention includes a topical testosterone formulation and methods for the making and use thereof. The formulation may be used by both men and women in a treatment regimen which achieves desired testosterone serum levels in the subject receiving treatment. As such, the formulation may be used to treat a variety of diseases or conditions that are thought to be responsive to testosterone supplementation therapy.

One specific advantage of the present testosterone formulation is its ability to achieve physiologic testosterone levels with a small volume. Daily application of as little as 0.5–1.0 grams of the preparation of the present invention has been found to achieve physiological levels of free testosterone, total testosterone, estradiol and DHT. By comparison, other topical testosterone gels currently on the market require a much larger volume to achieve the same effect. For example, 5–10 grams of Androgel® is applied daily to achieve therapeutic levels of testosterone (Swerdloff et al., J Clin Endocrinol Metab 2000 December;85(12):4500–10, Androgel® Insert, Solvay, Belgium Subsidiary [Unimed, Buffalo Grove, Ill.]).

The smaller volume (0.5–1.5 grams) presents several advantages. For instance, when a large volume of a testosterone gel is used, the inadvertent transmission of testosterone to a second individual is a problem that could easily occur and raises great safety concerns. The patient must exercise extreme caution in application and usage. A reported case of precocious puberty in a 2-year-old boy whose father was using the Androgel® on his arms and back indicates the need for caution in transference issues (Cutter, C.; J Am Board Fam Pract 14(1):22–32, 2001). The risk of such an occurrence is greatly reduced with the topical formulation of the present invention due to the small volume (0.5–1.5 grams) which is able to achieve therapeutic levels.

Further, the formulation of the present invention may be applied in the subaxillary area or below the underarm upon arising in the morning, which should further avoid this transmission. In men without a sexual partner, a small volume of the formulation can be applied directly to the scrotum. Thus, the gel of the present invention is comparable in safety profile to many of the transdermal patches which utilize an occlusive backing layer, as opposed to presenting the risks of transference associated with Androgel® and other topical testosterone replacement therapies which require large volumes applied to the skin (Wang et al., Clin Endocrinol (Oxf) 2001 June;54(6):739–50).

As discussed above, one problem with currently marketed testosterone replacement therapies is the metabolic conversion of testosterone to an estrogen, such as estradiol. Surprisingly, it has been found that a rapid conversion of free testosterone (FT) to DHT in preference to estrogen synthesis from aromatase activity, occurs when testosterone is delivered using the present topical formulation. This minimization of estrogen production is at least one reason why the present formulation is able to achieve physiologic, testosterone levels including FT and bioavailable T, with such small volumes. Simply put, more of the testosterone delivered to the serum either remains as testosterone or is converted to DHT, each of which has an androgenic effect. Additionally, because no significant increase in estrogen level occurs, the desired therapeutic objectives such as increased muscle strength, mood and sexual energy and drive in men and/or women may be achieved using a smaller testosterone dose.

The present topical testosterone formulation may include a variety of ingredients which provide the above-recited characteristics and properties, as well as others. In its most basic form, the formulation may include a poloxamer lecithin organogel (PLO) having admixed therein, an effective amount of arginine ingredient, an effective amount of a tocopherol ingredient, and a therapeutically effective amount of testosterone. Such a formulation has been found to provide a sustained release of testosterone through the skin of a subject, and achieve therapeutic, or physiologic levels of salivary and serum testosterone as shown in Table 3.

PLO is a stable compound and has not shown harmful side effects when applied to a patient's skin for prolonged periods. As recited above, PLO's are well known in the art and generally include at least the ingredients of a poloxamer, lecithin, and water. The particular amount of each specific ingredient included in the PLO may be varied, and several different specific formulations are known to those skilled in the art. Generally, the amount of poloxamer in a typical PLO is from about 5%w/w to about 20% w/w. While such PLOs may be used in the present invention, in one aspect, the PLO may be "modified" to contain a higher percentage of poloxamer. In one aspect, the amount of poloxamer may be about 20% w/w or greater. In another aspect, the amount may be about 30% w/w or greater. In yet another aspect, the amount of poloxamer may be from about 20% w/w to about 30% w/w of the PLO.

A variety of different poloxamer ingredients may be used in the PLO of the present invention. However, in one aspect, the poloxamer may be PLURONIC F-127 (BASF, Germany, Molecular Probes, Eugene, Oreg.). PLOs have been effectively used by physicians and pharmacists to deliver hydrophilic and lipophilic drugs transdermally across the stratum corneum for years. As recited above, poloxamers are generally block copolymers of polypropylene oxide, (PPO) and polyethylene oxide (PEO) segments in the sequence PEO-PPO-PEO. A number of poloxamers, such as those sold under the trade name PLURONIC by BASF are well-known for use in pharmaceutical carriers whose hydrophobic PPO segments aggregate, leading to the distinctive gelation seen at room temperature. The PPO aggregation is thought to form micelles, which liquefy at body temperature and serve to solubilize lipophilic drugs in aqueous media and allow their slow release (Dagani R., Chemical and Engineering News, Jun. 9, 1997).

Additionally, PLO is a versatile transdermal delivery carrier, and particularly well-suited for use in the present invention, because of its solubilizing capacity and because both hydrophobic and hydrophilic drugs can be incorporated into it. (Willimann et al., J. of Pharmaceutical Sciences, Vol. 81, No. 9, September 1992., p.B71–B74). The carrier used in the present invention is designed to effectively solubilize and suspend both testosterone and other active ingredients, sustain the release or delivery of the drugs through the skin, and raise serum levels of testosterone proportional to the dose administered. Oil-soluble compounds such as testosterone, tocopherols, and dehydroepiandrosterone (DHEA) are miscible within the lecithin phase, while water-soluble compounds such as L-arginine are miscible within the aqueous phase. Once each drug is incorporated into its respective phase, both phases are mixed together to form a composition that is rapidly absorbed through the skin.

The present invention contains a therapeutically effective amount of testosterone. In one aspect, the amount of testosterone may be from about 0.1% w/w to about 20% w/w of the formulation. In another aspect, the amount may be from about 5% w/w to about 10% w/w of the formulation. While several forms of testosterone may be used, in one aspect, the testosterone may be micronized. In another aspect, the testosterone may be "natural" testosterone, or "native" testosterone, for example, testosterone extracted from soybean, rather than a testosterone salt, or other derivative. Such testosterone USP, micronized for the present invention can be obtained, for example, from Professional Compounding Centers of America, Houston, Tex.

In addition to the carrier and testosterone, the formulation of the present invention includes an effective amount of arginine. Arginine, a naturally occurring basic amino acid, is a physiologic precursor of nitric oxide (NO) and is converted to NO through the action of nitric oxide synthase (NOS). There is a substantial body of evidence from animal experiments that a deficiency in NO may contribute to the pathogenesis of erectile dysfunction in men, among other diseases. It is thought that NO, a gas with intrinsic vasodilator properties, activates guanylate cyclase and in turn stimulates the formation of cyclic GMP or cGMP. This substance then acts as a second messenger, playing a pivotal role in vasodilatation and relaxation of corporal smooth muscle, the structural changes responsible for penile erection (Moncada et al., Pharmacol. Rev. 1991; 43:109–142). In one aspect, the amount of arginine may be from about 0.1% w/w to about 20% w/w of the formulation. In another aspect, the amount may be from about 5% w/w to about 10% w/w of the formulation Further, arginine, including L-arginine may be included in the present formulation in a variety of forms, including salt forms, chelated forms, etc. However, in one aspect, the arginine may be present as L-arginine monochloride.

Tocopherol is another ingredient which may be included in the topical formulation of the present invention in an effective amount. In fact, it is presently thought that the minimization of metabolic estrogen formulation may be due to the inclusion of a tocopherol ingredient in the present formulation. Applicant has discovered that the concomitant administration of either alpha-tocopherol, gamma-tocopherol or both, with the testosterone may provide significant aromatase inhibition, which in turn inhibits the aromatic conversion of testosterone to estrogen. Additionally, both alpha and gamma tocopherol have been shown to have potent antioxidant activity which has been shown to have significant benefits in the prevention of prostrate cancer, the prevention of heart disease and strokes. When applied topically these tocopherols possess both topical ultraviolet blocking activity equivalent to current sunscreens and also provide systemic antioxidant effects. (McVean et al., Mol Carcinog 1999 March, 24(3):169–76; Liebler et al., Carcinogenesis 2000 February; 21(2):221–5; Szulc et al., Pharmazie 1994 April; 49(4):295; Norkus et al., Photochem Photobiol 1993 April, 57(4):613–5; Kondo et al., Photodermatol Photoimmunol Photomed 1990 August; 7(4): 173–7).

Any amount of tocopherol that is sufficient to reduce or minimize the aromatic conversion of testosterone may be used. However, in one aspect, the amount of tocopherol included may be from about 0.1% w/w to about 20% w/w of the formulation. In another aspect the amount may be from about 2–10% of the formulation. In yet another aspect, the amount may be from about 5% w/w to about 10% w/w of the formulation.

Other ingredients may be optionally added to the topical testosterone formulation of the present invention which have an effect on testosterone producing tissue or metabolism, or which provide additional positive health benefits. By way of example without limitation, ingredients such as dehydroepiandrosterone (DHEA), melatonin, oxytocin, and progesterone may be included.

DHEA is known to provide a variety of positive health benefits, such as modulating diabetes and obesity, decreasing carcinogenesis or tumor growth, neural outgrowth, virus and bacterial infection, stress, cognitive function, hypertension, collagen and skin integrity, fatigue, depression, memory, and immune responses (Mohammed Kalimi and William Regelson [Eds], Walter de Gruyter, New York, 1990.). DHEA has also been used for the prevention of hyperplasia of the prostate (see for example U.S. Pat. No. 4,956,357, which is incorporated herein by reference). Oral DHEA has been shown useful for memory improvement and reversal of menopausal symptoms in women DHEA has been found to be safe in low doses of 10–25 mg applied topically per day, and has been found to be well absorbed through the skin and rapidly metabolized to its sulfate (DHEAS), androstenedione, and consequently to testosterone and estradiol (Sulcova et al., Physiol Res 2000;49(6): 685–93). Therefore, in addition to DHEA, other compounds thereof, such as dehydroepiandrosterone sulfate (DHEAS) may be used.

It has been further found that the addition of DHEA to the formulation of the present invention aids in the attainment of stable physiologic levels of free testosterone (FT), DHT, and DHEA, all of which decrease normally with aging (Schwartz et al., Mohammed Kalimi and William Regelson [Eds], Walter de Gruyter, New York, 1990). Specifically, these hormones act in concert to prevent the conversion of excess free testosterone to estradiol (E2) (Nawata et al., Endocrinol Jpn 1977 February; 24(1):41–5).

The effects of DHEA administration may be due to the effects of its conversion products such as estrogen and testosterone. When applied topically, 10–20 mg of DHEA are absorbed easily into the blood stream resulting in increases of both estrogen and testosterone in women and increased DHEA-S (the sulphated ester of DHEA) in men. Supplementation increases cognitive function, lowers LDL in both men and women, reduces obesity and is therefore potentially protective against heart disease (Weksler M E, BMJ 1996 Apr 6; 312(7035):859–60).

While any amount of DHEA which is effective in providing a significant positive health benefit without taking away from the efficacy or action of the testosterone may be included, in one aspect, DHEA may be included in an amount of from about 1% w/w to about 20% w/w of the formulation.

As stated above, in another aspect, the formulation of the present invention may include an effective amount of melatonin. Melatonin receptors are present in the human prostate epithelium. Melatonin treatment of 1 nM for 2–7 days was found to inhibit cell growth and markedly increase the percentage of non-viable cells in a culture of prostatic cells (Jones et al., Cancer Lett Apr. 14, 2000; 151(2): 133–143). While any amount of melatonin deemed to be effective which does not detract from the testosterone administration of the present invention may be included, in one aspect, the amount of melatonin may be from about 1% w/w to about 20% w/w of the formulation. In another aspect, the amount may be from about 5% w/w to about 10% w/w of the formulation.

As with melatonin, oxytocin an effective amount of oxytocin may be included in the formulation of the present invention. Oxytocin is thought to be involved in the pathophysiology of the prostate gland. Oxytocin is present in the mammalian prostate and plays a role in the male reproductive tract by both assisting sperm transport and modulating steroidogenesis. In the testis, oxytocin has been shown not only to modulate testosterone production but also to increase the activity of the enzyme 5 alpha-reductase which converts testosterone to DHT. Prostatic oxytocin concentrations are decreased by testosterone and increased following treatment with an antiandrogen such as Progesterone. Oxytocin treatment increases 5 alpha-reductase activity in the prostate thus creating a local feedback mechanism may act to control prostatic levels of DHT and hence prostatic growth. Preliminary findings also suggest that prostatic oxytocin levels are raised in tissue from men with BPH (Nicholson H D et al, Adv Exp Med Biol 1995;395:529–38).

The specific amount of oxytocin added to the formulation of the present invention may be any amount determined to be effective by one of ordinary skill in the art, which does not reduce the efficacy or action of the testosterone in the formulation. However, in one aspect, the amount of oxytocin may be from about 1% w/w to about 20% w/w of the formulation. In another aspect, the amount may be from about 5% w/w to about 10% w/w of the formulation.

An effective amount of progesterone may also be included in the formulation of the present invention. Progesterone has been shown to provide a variety of positive health benefits, including cancer prevention. (Mobbs et al., Prostate 1990;16 (3):245–51). In clinical studies prostate exams and PSA levels do not indicate any notable affect on prostatic volume. Ongoing research indicates that altered testosterone/ estrogen ratio associated with aging may affect the production of PSA glycoprotein. If progesterone level is also lowered as well, this may provide a clue as to possible early prostatic carcinoma. Adding progesterone as part of the invention therefore may offer an approach to prevent prostate cancer in aging men (Brown et al., Biol Repod 1984 February;30(1):67–73).

Progesterone is particularly an important component of the formulation, when the formulation is used to temporarily and reversibly reduce sperm count (i.e. as a contraceptive). While any amount of progesterone may be included in the formulation which achieves a desired result without reducing the efficacy of the testosterone, in one aspect, the amount of progesterone may be from about 1% w/w to about 20% w/w of the formulation. In another aspect, the amount may be from about 5% w/w to about 10% w/w of the formulation.

The present invention additionally encompasses methods for the making and use of a topical testosterone formulation. In one aspect, a method for treating a disease or condition responsive to testosterone therapy may include the step of administering a topical testosterone formulation as disclosed herein. In one aspect, a regimen or routine of daily administration may include application of the formulation in the amounts of 0.5–1.5 grams each morning, to the subaxillary or underarm area. The use of 0.5 to 1.5 grams of the formulation one time per day may yield stable levels of testosterone which peak in the morning, mimicking the normal physiological variations in testosterone level.

Specific aspects of a treatment regimen, including the amount of testosterone and other contents included in the present formulation may be customized to achieve optimal treatment results for a specific disease or condition in a specific individual. The particular ingredients and amount thereof may be determined using the knowledge of one ordinarily skilled in the art without undue experimentation, based on an evaluation of the subjects particular symptoms and physical condition. However, in one aspect, the dosage may be from about 0.5 g to about 2 g of the formulation. In another aspect, the dosage may be from about 0.5 g to about 1 g of the formulation. In yet another aspect, such a dosage may achieve physiologic levels in the subject. Further, such physiologic levels may in one aspect, be serum levels of about 600 ng/dl to about 1200 ng/dl. The particular time frame of the treatment routine may extend for any time necessary to achieve a specific result as determined by one of ordinary skill in the art. However, in one aspect, the regimen may extend for at least about 30 days.

The time frame for achieving a specified testosterone serum level will depend on a variety of factors, such as the amount of the formulation applied, and the surface area of application. However, in one aspect, peak serum testosterone levels may be achieved within about 24 to about 36 hours after application. The flux rate (i.e. penetration or delivery rate) of testosterone through the skin may be enhanced by the specific physical properties of the present formulation, which are determined in party by its method of preparation.

In one aspect, a method of making the present formulation may include the use of an ointment mill. The mixture of testosterone with the carrier results in the formulation of micelles which interact with the regularly arranged layers of lipids upon skin contact and slip therethrough, delivering the testosterone. The pressure applied to the poloxamer micelles by the rollers of the ointment mill decreases the size of the micelles to a point that penetration thereof through the skin is increased as compared to larger micelles. As such, the penetration of the testosterone is effectively increased. Further, running the topical formulation through the ointment mill until it is smooth and non-granular not only enhances penetration, but makes it softer and more comfortable for the patient. In one aspect, the topical formulation may be passed through the ointment mill at least 3 times, or until substantially no testosterone crystals remain visibly or tactily detectable. Further, as alluded to above, in addition to the tocopherol ingredient, the penetration rate of the present topical formulation may further aid in minimizing the aromatic conversion of testosterone to an estrogen.

A number of adverse or detrimental effects, some of which are life-threatening, have been known to result from testosterone deficiencies, or other hormonal imbalances. For example, there has been thought to be an inverse relationship between tumor volume, as defined by PSA level, and 5 alpha-reductase activity, as defined by DHT level. Therefore the maintenance or decrease in T/DHT ratio may protect men from prostate cancer. Androgens may therefore be "protective" in the male prostate (Kuhn et al., Clin Endocrinol Metab 1984 February;58(2):231–5). Free testosterone, DHT, testosterone and sex hormone binding globulin (SHBG) did not vary with age, however, older men had higher estradiol levels (Hayes et al., Eur J Cancer Prev 1992 April;1(3):239–45). The inhibitory effect of antiandrogens on prostatic cell proliferation may be the result of the suppression of conversion of T to DHT by progesterone and estradiol, as well as decreased androgenic support and decreased epithelial growth factor or EGF release and expression. Testosterone in combination with progesterone may therefore be important in preventing cancer of the prostate. DHT although it is involved in prostate enlargement as currently postulated, may require the presence of other hormones such as E2 for it to act as a major initiator of prostate cancer (Tilakaratne et al., supra).

Imbalanced androgens can additionally provide the primary signal for the onset of DNA synthesis and cell division in normal prostate tissue resulting in benign prostatic hyperplasia (BPH). The high affinity melatonin receptors in the human benign prostate epithelial cells, which affect cell growth and viability may be protective against benign prostatic hyperplasia and prostrate cancer (Robertson et al., Prostate 1995 January;26(1):28–34.). The melatonin receptor in prostate cells is sensitive to T levels and DHT levels and tends to prevent the enlargement of the prostate if levels of melatonin are adequate (Gilad et al., Clin Endocrinol Metab 1997 August; 82(8):2535–41.).

While it is true that prostate cancers are usually androgen dependent, induction may be related more to E2 and progesterone levels than T levels (Sciarra et al., Arch Androl 2000 May–June;44(3):213–20.). There are minimal progesterone receptors in the stroma of either benign or malignant prostates and progesterone derivatives can act as an inhibitor of 5-alpha-reductase in prostate cancer lines. (Srinivasan et al., Microsc Res Tech 1995 Mar. 1;30(4):293–304).

Many of the above-recited conditions and diseases may be effectively treated or prevented by the preparation of the present invention, and its ability to raise circulating testosterone and DHT to therapeutic levels and achieve a proper balance of testosterone to estrogen. Additionally, other diseases or conditions, may be treated using the topical testosterone therapy, such as AIDS Wasting Syndrome (AWS), the prevention of prostate cancer, post-anabolic steroid abuse, hypogonadism, somatopause, andropause, viropause, anemia, kidney disease, benign prostatic hyperplasia, acne, infertility, constipation, dry eyes, periodontal disease, diabetic retinopathy and other retinopathy, Lupus Erythematosis or other autoimmune diseases, decreased bone density or osteoporosis, high cholesterol, heart disease, hyperlipidemias, and anginas. Further, testosterone supplementation therapy from the present invention may significantly increase muscle strength, mood and energy in men and women, increase insulin-like growth factor in serum and saliva, cause a temporary decrease in sperm count, and increase the penis size in prepubertal boys and hypogonadal men with micropenis when administered. Additional information on a number of these diseases or conditions is recited below.

(a) AIDS Wasting Syndrome

Testosterone and low serum DHEAS has been associated with AIDS wasting syndrome and various HIV illness markers, including viral load (Evans et al., Semin Oncol. 1998, 2 (suppl 6):112–122; Kopicko et al., Int J STD AIDS. 1999;10:817–820; Abrams D. The AIDS Reader 11(3): 149–156, 2001,;Javanbakht et al., abstract, ENDO 2000; Sattler et al. 1998;18:246–51; Ferrando et al., J Acquir Immune Defic Syndr 1999 October 1;22(2):146–54; Arver et al., J Androl 1999 September–October;20(5):611–8). In a recently reported clinical study, significantly more HIV-positive male patients who had decreased levels of testosterone were found to have HIV wasting, opportunistic infections and CD4 lymphocyte counts below 200/microliter than those with normal testosterone levels. In HIV-infected women and in hypogonadal men, the administration of testosterone has been shown to increase fat-free mass, augment lean muscle mass, and improve quality of life (increased energy, libido and sense of well-being) (Javanbakht et al., J Clin Endo. 2000;85: 7: 2395–2401).

The testosterone to DHT ratio in HIV-infected people is very similar to that in uninfected people. Thus, this illustrates that the activity of 5-alpha reductase is not inhibited by the presence of HIV infection. Rather it is a decrease in total testosterone, free testosterone and DHT that is associated with AIDS wasting syndrome (Dobs et al., J Clin Endocrinol Metab 1996 November;81(11):4108–12). Therefore, testosterone replacement therapy which effectively raises circulating levels of free testosterone, total testosterone and DHT would be effective in treating AIDS Wasting Syndrome (Dobs et al., J Clinic. Endocrinol. Metab. 1996; 81:4108–12; Javanbackht et al., J Parenter Enteral Nutr. 1999;23:S195–S201).

Transdermal testosterone replacement can reverse some of the wasting changes including loss of muscle mass in both men and women with advanced AIDS (Mazer, N., Watson study 2000; Javanbakht et al., 2000, supra). Treatment is directed toward restoring normal energy, weight, appetite and moods in men and/or women with AIDS Wasting Syndrome (AWS) or the loss of muscle mass in HIV infected children and/or adults.

(b) Hypogonadism, Somatopause, Andropause, Viropause and Adrenopause

Transdermal testosterone replacement therapy has similarly been shown to be an effective treatment for hypogonadism and other conditions associated with low testosterone levels in men: somatopause, andropause, viropause, and adrenopause. (Swerdloff et al., J Clin Endocrinol Metab 2000 December;85(12):4500–10; Cherrier M., abstract, Endocrine Society, New Orleans, July 1998; Carani et al., Arch Sex Behav 1990;19:223–34; Morley et al., Med Clin North Am. 1999;83:1279–1289; Ellyin et al., abstract, S Cruz Department of Medicine, The Chicago Medical School and Swedish Covenant Hospital, North Chicago, Ill. Endo 2000; Meacham R., Infect Urol 14(2):30, 2001; Heaton et al. Can J Urol 2001 April 8;8(2):1213–22).

(c) Periodontal Disease

The etiologies of periodontal endocrinopathies are diverse; nonetheless, periodontal pathologies may be a consequence of the actions and interactions of sex steroid hormones on specific cells found in the periodontium or supporting tooth tissue. (Mariotti A., Crit Rev Oral Biol Med 1994; 5(1):27–53). The action of the hormone replacement therapy of the present invention on periodontal disease and the production of DHT in the gingival fibroblasts is fascinating. Periodontal pathogens metabolize steroid hormones which could contribute to their nutritional requirements and host evasion mechanisms, by forming capsular proteins; their culture supernatants stimulate the synthesis of physiologically active steroid hormones by fibroblasts, which aid inflammatory repair and antimicrobial action through local nitric oxide release. (Soory M., Curr Drug Targets 2000 December; 1(4):309–25).

The present invention could further aid in treating periodontal disease. The increase in DHT on a local level in the gingival fibroblasts may alter the modulatory mechanisms involved, in periodontal disease presentation during altered hormonal states and DHT may be involved in the healing responses in the inflamed periodontium. The modulatory effects of estradiol and DHT on androgen metabolism may influence disease presentation and the progress of healing responses in the inflamed periodontium. This effect is augmented by DHT stimulation with minocycline (Tilakaratne et al., Periodontol 1999 September;70(9):1017–25; Soory et al., Arch Oral Biol 2000 April;45(4):257–65).

(d) Prostate Cancer and Benign Prostatic Hyperplasia.

Normal prostatic function appears to depend on the capability of testicular and prostatic tissue to provide an appropriate ratio of testosterone to estrogens. Intraprostatic conversion of free T to DHT 2 within the prostate causes hyperplasia and hypertrophy of the gland (Randall V A., supra). A hormonal mechanism underlying Benign Prostatic Hyperplasia (BPH) is most likely, since the presence of testosterone or dihydrotestosterone (DHT) is necessary for the development of hyperplasia; BPH is not seen in eunuchs (Bartsch, W., Maturitas 1980 July; 2(2):109–18; Bartsch et al., Eur Urol 2000 April; 37(4): 367–80; Osterling et al., JAMA 1993; 270:860).

In one aspect, the topical formulation of the present invention could further aid in treating prostatic diseases. The modulatory effects of estradiol, high DHT and progesterone on androgen metabolism may influence disease presentation and the progress of healing responses in the prostatic epithelium. Progesterone inhibited the formation of DHT and androstenedione by 10-fold and 3-5-fold at effective inhibitory concentrations (n 4; p<0.001), when 14C-testosterone was used as substrate. Similarly, when 14C-4-androstenedione was used as substrate, progesterone decreased the yields of testosterone, DHT, and estradiol. These results reinforce the potentially anti-anabolic and anti-estrogenic roles of estradiol and progesterone, respectively. Circulating progesterone may act as a blocking hormone on testosterone conversion to DHT from the action of the local 5 alpha reductase enzyme.

The enlargement of the prostate (BPH) that takes place in later years in adult males is generally coincident with increases in modulating hormones eg. oxytocin. Prostatic oxytocin levels are decreased by testosterone and increased following treatment with anti-androgens such as progesterone. Decreases in the levels of DHEA and DHEA-S in the blood are also associated with BPH. At the same time there are apparent increases in estrogen dominance as testosterone levels fall resulting in increased E2/T ratios. Imbalance in androgens can signal the onset of cellular division in normal prostate tissue resulting in hyperplasia. Melatonin receptors in prostatic epithelial cells may be protective against BPH by their modulation of oxytocin activity-decreasing 5 alpha reductase activity. Increased estradiol (E2) levels are believed to be responsible for stimulation of DHT formation from free testosterone via 5 alpha reductase-2 (5 AR-2), resulting in prostatic stromal and epithelial cell growth. This may explain the apparently benign effects of the present invention on prostatic tissue after 3 years of regular application as shown in Table 1 and FIG. 2.

An elevated DHT level has been a source of some concern, because of its perceived effects on prostate growth (Cutter C., supra). Nonetheless, researchers reviewing the effects of the Testoderm® scrotal patch and other nonscrotal patches have found few problems with prostatism regardless of DHT levels. (Testoderm® TTS, Testoderm®, and Testoderm® with adhesive, package inserts, Mountain View, Calif. Alza Pharmaceuticals, 1998; De Lignieres, supra; Meikle et al., Urology 1997; 49:191–6; Schaison et al., Niesch-lag E editor, Behre H M., New York: Springer Verlag, 1990:155–64; Arver et al., Clin Endocrinol (Oxf) 1997; 47:727–37; Bals-Pratsch et al., Acta Endocrinol (Copenh) 1988;118:7–13). Other researchers have actually shown a 15% decrease in prostate size in patients using a pure DHT gel (De Lignieres, supra, Ly et al., J Clin Endocrinol Metab 2001 September;86(9):4078–88).

If DHT is produced in the prostate tissue through the action of 5AR-2, and accumulates within the gland there is prostatic growth (and increased PSA) (Wilson J D., Am J Med 1980 May;68(5):745–56). If DHT produced in the skin by the action of 5AR-1, (as we postulate occurs with the present invention) antagonizes the production of DHT in the prostate, by its feedback action on 5-alpha reductase-2, there may not seem to be any apparently notable effect on PSA. Thus it could be argued that DHT does not seem to cause prostatic growth on its own (Rittmaster R. S., Am J Med 1995 January 16;98(1A):17S-21S). Some androgenic modulating effects may be mediated by supraphysiologic levels of circulating dihydrotestosterone acting as a hormone regulator (Wilson J. D., supra).

Further, although it has been widely suggested that elevated androgen levels may be critically involved in the genesis of prostate cancer, and despite the dependency of the normal prostate and of most prostatic cancers upon androgens and the fact that tumors can be produced in some rodent models by androgen administration, some have argued that, contrary to prevalent opinion, declining rather than high levels of androgens probably contribute more to human prostate carcinogenesis and that androgen supplementation can lower the incidence of the disease (Prehn et al., supra).

Prehn et al. argue that the growth of androgen-independent prostate cancers might be reduced by the administration of androgens. The use of the present invention is effective in the prevention of prostate cancer. Hidden prostate cancer is related more often to low serum testosterone levels not high testosterone levels (Morgentaler et al., JAMA 1996 December 18 276:23 1904–6; Heikkila et al. Cancer 1999 July 15;86(2):312–5). DHT levels tended to be lower among those with more advanced tumors. There was an inverse relationship between tumor volume, as defined by PSA level, and 5 alpha-reductase activity, as defined by DHT level, and the testosterone/DHT ratio (Gustafsson et al, supra).

An optional embodiment of the present invention containing melatonin may further protect against prostate cancer. The high affinity melatonin receptors in the human benign prostate epithelial cells, which affect cell growth and viability may be protective against cancer (Gilad et al., supra; Marelli, et al., Prostate 2000 November 1;45(3): 238–44; Shiu et al., Biol Signals Recept 2000 May;9(3–4): 172–187; Andersonet al., Hum Reprod 1993 November; 8(11):1819–22). Melatonin receptors are present in the human prostate epithelium. Melatonin treatment of 1 nanomole (nM) for 2–7 days was found to inhibit cell growth and markedly increased the percentage of non-viable cells in a culture of prostatic cells (Jones et al., supra).

Figure 3A:
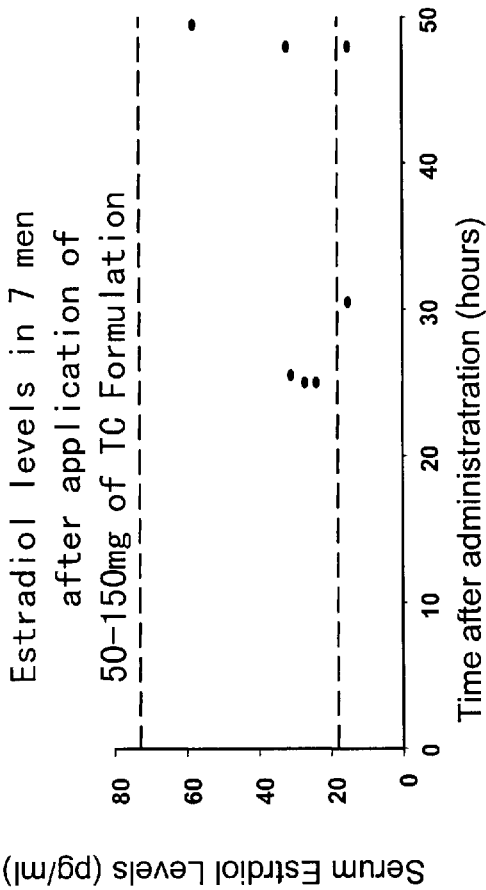
FIG. 3A shows the serum estradiol levels (normal range of 18–73 pg/ml) of 7 male patients measured after administration of daily administered doses (0.5 cc–1.0 cc) of a topical testosterone formulation containing about 10% w/w testosterone in accordance with one aspect of the present invention. The normal estradiol range is indicated by the two dashed lines.
Figure 3B:
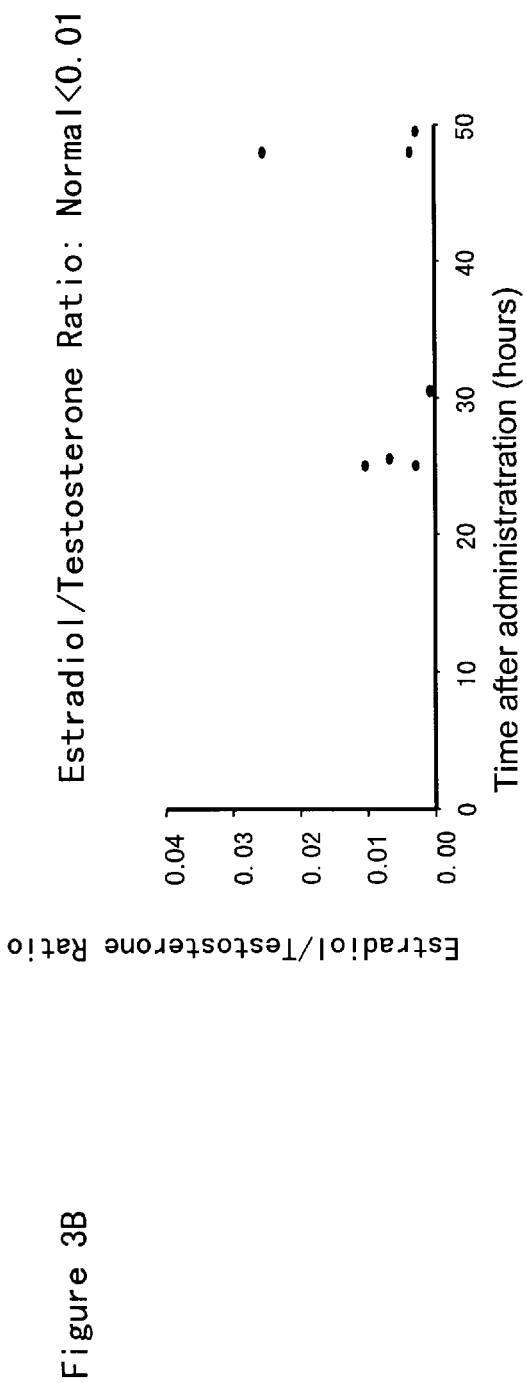
FIG. 3B represents the ratio of serum estradiol to testosterone [total T] in 7 men measured after administration of daily doses (0.5 cc–1.0 cc) of a topical testosterone formulation containing about 10% w/w testosterone in accordance with one aspect of the present invention.

As such, the present invention presents a unique approach to the prevention of cancer of the prostate in aging men. Sex steroids are responsible for cellular changes in the prostate gland however, it may not happen as previously thought. Androgens provide the primary signal for the onset of DNA synthesis and cell division in normal prostate resulting in benign prostatic hyperplasia (BPH). It is possible, however, that androgen mitogenic activity is in part indirect and mediated by peptide growth factors and E2 (Sciarra et al., supra). Treatment with the preparation of the present invention does not significantly affect the amount of E2 (See FIG. 3A) or the E2/T ratio (see FIG. 3B). These studies point to the potential action of the present formulation as a "preventive" therapy for BPH and prostate cancer in aging men.

(e) Increase in Insulin-Like Growth Factor (IGF-1) and Bioavailable Testosterone Concentration in Both Serum and Saliva.

The present invention, by its increase in testosterone can cause an increase in insulin-like growth factor (IGF-1) and in bioavailable testosterone concentration in both serum and saliva (Meikle et al). Testosterone and DHT increased the IGF-I mRNA level 30 and 40 times, respectively, relative to hypophysectomized control animals (Sahlin et al., J Steroid Biochem Mol Biol 51: 57–66 (1994). In men, rhGH responsivity increased over time in men on androgen substitution, but plateaued in men without androgen substitution, therefore proving that adequate androgens are essential for GH to be effective (Span et al., J Clin Endocrinol Metab 2000 March;85(3):1121–5). The main physiologic action of GH is to stimulate insulin-like growth factor.

There is a direct effect of IGF-I on sex hormones and sex organs in the male. With aging, IGF-1 levels decrease along with loss of muscle strength, decrease in bone mineral density and body composition, including lean mass and fat mass. Elderly men have a deficiency of non-SHBG-Bound-T which correlates very closely with low levels of bioavailable testosterone. (van den Beld A W, et al. J Clin Endocrinol Metab 2000 September;85(9):3276–82). Major age-related changes in the hypothalamic-pituitary-gonadal axis also occur at the level of the testes and are manifested by decreased responsiveness to bioactive luteinizing hormone (Tenover J S et al., supra). The resulting effects are that there is a progressive rise in luteinizing hormone and follicle-stimulating hormone without a physiologic increase in testosterone associated with aging (Laron et al., Eur J Endocrinol 1998 February;138(2):176–80). The stimulation of IGF-1 with transdermal testosterone delivered in a circadian pattern (increase during the night and decrease during the day) results in a concomitant increase in the size of the testes and penile length (Laron et al, supra; Cooke R R, et al. Clin Endocrinol (Oxf)1993 August;39(2):163–71).

The measurement of free testosterone level in saliva may have a more important role than total testosterone both in the diagnosis of diseases characterized by androgen deficiency and in hyperandrogenic status (Corradi et al., Orv Hetil 1998 August 23;139(34):2021–4). The measurements of salivary testosterone reflect plasma testosterone and may be a useful noninvasive method of assessing levels of free or "circulating testosterone" (Khan-Dawood et al., Am J Obstet Gynecol 1984 Feb. 15;148(4):441–5).

A preferred embodiment of the present invention containing DHEA may further be used to affect androgens and their regulating hormones. Transdermal DHEA has been found to raise follicle stimulating hormone or FSH, LH, lower T levels, lower Lp(a), lower cholesterol LDL levels in diabetics (Sulcova et al., Physiol.Res.2000; 49:685–93; Coleman et al., Diabetes 31: 830–833; Coleman et al., Diabetes: 33: 26–32 1984; Rizza et al., Am J Physiol 240: E630–E639, 1981; Morgan et al., Diabetes 12: 115–126, 1963; Nestler et al., J. Clin Endocrinol Metab, 64: 180–184, 1987; Veldhuis et al., In: Veldhuis J, Giustina A, eds. Sex Steroid Interactions With Growth Hormone. New York, NY: Springer-Verlag Inc; 1999:93–121).

(f) Erectile Dysfunction.

The present invention acts to improve erectile dysfunction by enhancing libido, frequency of sexual acts and sleep related erections (Shabsigh R., World J Urol 1997;15(1): 21–6). Testosterone also causes a decrease in fat mass (abdominal obesity) and an increase in lean body mass which plays a role in preventing erectile dysfunction in men with increased waist sizes. (Herbst K L, et al., abstract, Endo 2000; Rimm, et al., abstract 1073, American Urological Association 95th Annual Meeting; Atlanta, Ga.; April 29 May 4, 2000. As well as FT, there are important metabolites of testosterone which play a major role in male sexual behavior. Dihydrotestosterone or DHT level is a major predictor of sexual activity, particularly orgasms, in young men. DHT seems to be the most important predictor of the frequency of orgasms in non-human primates as well as rodents (Mantzoros C et al., BMJ May 20, 1995;310:1289–91). The topical testosterone formulation of the present invention increases the level of free testosterone and DHT in saliva and serum (data not included). DHT is the active androgen in the prevention of erectile failure. Erectile enhancement effect due to the presence of L-arginine may be mediated by changes in nitric oxide synthase levels in the penis (Lugg et al., Endocrinology 1995 April;136(4): 1495–501). Free or active testosterone level can provide an adequate screening test for sexual drive and reflects DHT level in the serum, however, DHT itself binds more avidly with the androgen receptor. (Mantzoros et al., supra; Carani et al., Arch Sex Behav 1990;19:223–34; Ansong et al., J Urol 1999 September;162(3 Pt 1):719–21; Pirke et al., Acta Endocrinol (Copenh) 1975 June;79(2):357–65).

One study illustrates that erectile dysfunction correlates with alcohol consumption and sedentary lifestyle (Rimm et al, supra). Alcohol abuse will lower DHT which can be corrected by the use of the preparation of the present invention (Gustafsson et al., supra). Additionally, observations as part of the studies conducted with the preparation of the present invention indicated that treatment with the preparation of the present invention increases the frequency of early morning erections and raises DHT very effectively.

(g) Osteoporosis or Decreased Bone Density.

The preparation of the present invention acts to decrease bone density or osteoporosis through the action of increased DHT, FT and non-SHBG-T on bone mineral density (BMD). These parameters of bioavailable tesosterone were more positively related with muscle strength and total body BMD than total testosterone (van den Beld, et al.,supra). Androgens (FT, DHT) can stimulate human osteoblastic cell proliferation in vitro, and induce expression of the osteoblast-line (more bone build up) by an androgen receptor mediated mechanism (Kasperk et al., Endocrinology 124: 1576–8 (1989); Leifke et al., Eur J Endocrinol 1998;138:51–8; Bellidoet al., J Clin Invest 95: 2886–95 (1995); Seeman E., Baillieres Clin Rheumatol 1997;11:613–29; Wang et al., Clin Endocrinol (Oxf) 2001 June;54(6):739–50).

(h) Lowering of Cholesterol Levels.

The lowering of LDL cholesterol levels by the action of the testosterone of the present invention on Apo B and increases in HDL improves lipid profiles (Coleman et al., 1983, supra; Coleman et al., 1984, supra; Rizza et al., supra; Morgan et al., supra; Nestler et al., supra; Veldhuis et al., supra; Segal et al., Lipids and Dyslipoproteinemia, In: Henry J B (ed), Clinical diagnosis and Management by Laboratory methods, Saunders, Philadelphia, 1984, pp. 180–203; Barrett-Connor EL., Diabete Metab 1995;21:156–61; Barrett-Connor et al., New England Journal of Medicine 315(24): 1519–24, 11 December 1986; Zgliczynski et al., Atherosclerosis 1996;121:35–43; Friedl et al., Metabolism 1990;39:69–74; Nestler et al., J. Clin Endocrinol Metab, 66: 57–61, 1988. [Abstract only]; Nestler et al.,1989. [Abstract only]; and U.S. Pat. No. 4,920, 115:Method for lowering LDL cholesterol in blood using DHEA). This controversial action of testosterone on lipids, augmented by the addition of DHEA has not yet been proven (Parker et al., Science 208: 512–513, 1980; Ben-David et al., Proc Soc Exp Biol Med, 125; 1136–1140, 1967). As percutaneous DHT administration is a relatively safe modality of androgen replacement therapy as far as atherogenicity is concerned (Vermeulen et al, Maturitas 1985 September;7(3): 281–7), the preferential conversion of this invention to DHT may have an anti-atherogenic effect.

(i) Heart Disease.

Several studies have shown that an increased incidence of heart disease occurs in men with low testosterone, DHT and DHEA levels (Swartz et al., J Am Geriatr Soc 1987;35:39–44; Barrett-Connor et al., N. Eng J Med, 1986, 315: 1519–1524; Schwartz et al., supra; Slowinska-Srzednicka et al., Atherosclerosis 1989 October;79(2–3):197–203). Serum testosterone levels were about 90 ng/dl lower in patients who had suffered myocardial infarctions than in those who had not (Swartz et al., supra). Routine use of Testosterone supplementation may be helpful in decreasing deterioration in men after myocardial infarction (Shippen et al., Pub. M. Evans and Company, Inc. New York, 1998; 79–97). Transdermal testosterone therapy in men with chronic stable angina leads to an improvement in objective measures of myocardial ischemia and concomitant improvement in quality of life scores (English K M, et al. Circulation 2000; 102:1906–11). The preferred embodiment of the preparation of the present invention containing DHEA may further reduce the incidence of heart disease as decreased levels of plasma DHEA-S may promote the development of coronary atherosclerosis in men (Slowinska-Srzednicka et al., supra).

(j) Cognitive Function.

The present invention may improve cognitive function in men, particularly in the area of spatial ability, depression and memory. Free testosterone stimulates the sexual drive in both men and women through effects centrally on the serotonin transporter (Fink et al, Behav Brain Res. 1999; Nov 1; 105(1): 53–68.). Increased sexual arousal and sexual enjoyment were associated with testosterone administration regardless of sexual status (Alexander et al. Horm Behav 1997 April;31(2):110–9). Testosterone may also enhance verbal fluency in hypogonadal men and may influence some aspects of cognitive function (Alexander et al. Horm Behav 1998 April;33(2):85–94).

The ratio of DHT/testosterone serum correlates significantly with decreased sexual aggression (Christiansen et al., Neuropsychobiology 1987;18(1):27–36; Christiansen et al., Horm Behav 1987 June;21(2):170–80). Testosterone has been proven to enhance libido, and to increase both the frequency of sexual acts and sleep-related erections (Dobs et al., supra). Androgen administration to eugonadal men with erectile dysfunction may activate their sexual behavior without enhancing erectile capacity and without effects on mood and psychological symptoms (Javanbackht et al., supra).

The action of testosterone on the brain to stimulate serotonin is mediated by its conversion to estradiol by aromatase activity (AA). (Fink G, et al. supra).

(k) Penis Size

Testosterone cream has been found effective in increasing the penis size in prepubertal boys and hypogonadal adult men with micropenis (Klugo et al., J Urol 1978 May;119 (5):667–8; Danish et al., Johns Hopkins Med J 1980 May;146(5):177–84). Testosterone influences penile growth, possibly as a result of extracellular stromal expansion by its action on androgen receptors in the penile corporeal bodies (corpus cavernosus) (Bin-Abbas et al., Pediatr 1999 May;134(5):579–83; Godec et al., Urology 1985 September;26(3):237–9). Topical testosterone also probably causes penile growth via its systemic action, via IGF-1 and not merely through its local effect (Jacobs et al., Urology 1975 December;6(6):708–10). The stimulation of IGF-1 with transdermal testosterone delivered in a circadian-like pattern results in an increase in the size of the testes and penile length (Laron et al, supra; Cooke RR, et al., supra). Penile growth cessation is mediated by mechanisms other than down regulation of the androgen receptor in adolescence. Early administration of androgen to prepubertal male individuals with low serum or salivary testosterone results in a longer phallus in adulthood (Baskin et al., J Urol 1997 September;158(3 Pt 2):1113–8; Rilling et al., Steroids 1996 June;61(6):374–8).

(l) Decreased Sperm Count.

Testosterone replacement has also been thought to suppress sperm counts in a reversible fashion (McLachlan, R I., Contraception 2000;62:73–78; Sjogren et al., Contraception 2001 July;64(1):59–65; Lobel et al., Acta Urol Belg 1989;57 (1):117–24; Aribarg et al, J Med Assoc Thai 1996 October;79(10):624–9). A combination of a patch and a progestational agent have been used effectively to suppress sperm production (Hair et al. J Clin Endocrinol Metab November 1;86 (11):5201–5209). In a limited study using the preparation of the present invention, two men were found to have decreased sperm densities within three months of use.

Two men who had low or infertile sperm counts (poor motility or abnormal spermatic forms) were evaluated. Baseline sperm counts were obtained before supplementation with the present topical testosterone formulation at a dose of one gram per day for a period of 1–8 months. After use of this topical cream for 8 months followed by stimulation with human chorionic gonadotropin (HCG), for one month, one man had a rise in his sperm count from less than 30,000 to over 2 million sperm (lower limit of fertility) with a subsequent normal semen analysis, when the baseline sperm analysis for this man had shown many abnormal sperm forms and a decreased sperm motility. The other man after only two months of use had an apparent increase in the volume of his ejaculate from 2–4 ml (double) with a considerable decrease of his sperm count from 2,000,000 to <50,000. The second man preferred this method of fertility control and did not use HCG.

(m) Testosterone Cream in MPLO Use in Renal Failure With Hemodialysis

Figure 5:
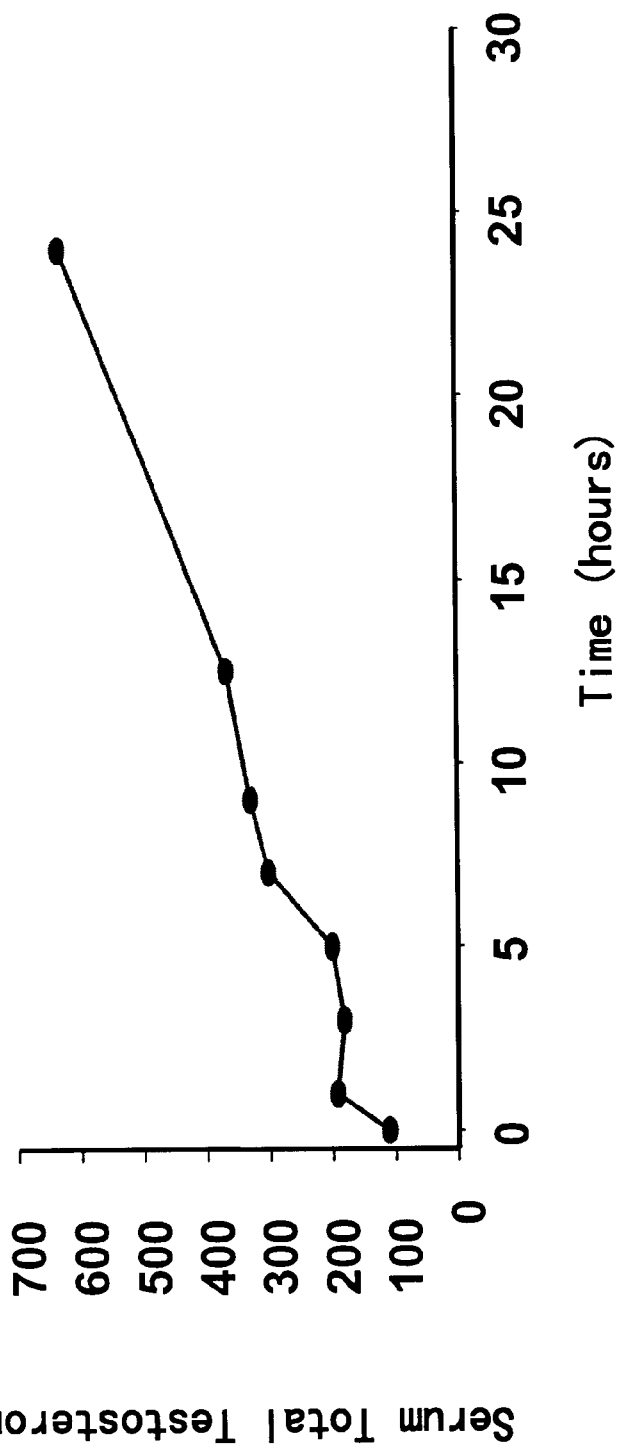
FIG. 5 illustrates the pharmacokinetics (change in serum concentration of total testosterone over time) of a single dose of a topical testosterone formulation containing about 10% w/w testosterone in accordance with one aspect of the present invention, administered to a single subject.

Rosas and associates documented a high prevalence of erectile dysfunction among 302 patients on hemodialysis (Rosas et al., American Urological Association 95th Annual Meeting; Atlanta, Ga.; April 29–May 4, 2000. Abstract 660). In men on hemodialysis, serum levels of total and free testosterone were significantly reduced compared with the controls (P<0.001), whereas the serum estradiol (E2) level was significantly elevated in men on hemodialysis (P<0.001) (Hayami et al., J Androl 2000 March–April;21 (2):258–61). Treatment for declining testosterone levels and high estradiol/testosterone ratios can be treated with hormone replacement therapies that effectively raise the serum levels of testosterone while lowering E2. The preparation of the present invention raises serum T (FIG. 5A) and DHT (data not shown) levels to physiological levels without increasing E2.

(n) The Present Formulation and Post Anabolic Steroid Abuse

New findings regarding the molecular basis of activation of the androgen receptor (AR) by DHT (Mantzoros et al., supra) and the importance of tissue conversion of circulating testosterone to dihydrotestosterone (DHT) and estradiol. (E2) support the view that supraphysiological doses of anabolic steroids do have a definite, positive effect on muscle size and muscle strength (Wu F C. Clin Chem 1997July;43(7):1289–92). Despite side effects which include:increased transaminase serum levels, changes in lipid profile, hypertension, jaundice, hepatic carcinoma, tendon damage, psychiatric problems, reduced fertility and gynecomastia plus suppression of the hypothalamic-pituitary-gonadal axis, it is unlikely that millions of athletes in Europe can "be persuaded to curtail their use" (Mottram D R, George A J. Baillieres Best Pract Res Clin Endocrinol Metab 2000 March;14(1):55–69; Ritsch M, Musshoff F., Sportverletz Sportschaden 2000 March;14(1):1–11).

In 1996, in the US, it was estimated that about 3 million male and female athletes had used androgenic steroids, which according to a Canadian study are "largely benign and reversible" in moderate doses. (Street C, Antonio J, Cudlipp D. Can J Appl Physiol 1996 December;21(6):421–40). Unfortunately, young men who have used high doses of exogenous steroids for more than several months find that after they stop, they have problems with their sexual behavior. Antagonism of LH secretion in the pituitary seems to occur from the central action of excess testosterone conversion by aromatase into estradiol. (Bagatell C J et al. J. Clin Endocrinol Metab 1994 June;78(6):1520). These same athletes may have inadvertently created secondary hypogonadism. The results of decreased spontaneous erections become associated with significant decreases in the frequency of sexual desire, sexual fantasies and intercourse as early as 6 weeks after cessation of suprphysiologic anaobolic steroid use. Many of these young men can be helped with transdermal androgen replacement therapy and HCG injections plus clomiphene to restore bioavailable testosterone (non-SHBG-bound levels) to normal (Tenover J S, et al. J Clin Endocrinol Metab 1987 December;65(6):118–26).

C. Examples

The present invention may be further illustrated by reference to the following examples:

EXAMPLE 1

A Specific Embodiment

One specific embodiment of the present invention is prepared as a hydrogel in the following manner. In order to prepare a total of 100 grams of the formulation the following steps are performed: 5 cc of ethoxy diglycol plus 5 cc of absolute ethyl alcohol are used to wet 10 grams of micronized testosterone USP powder in a liter beaker. One gram of dihydroepiandrosterone (DHEA), micronized, USP (Prof. Cmpd. Ctr. America) is added and stirred in thoroughly. The stirring creates a white creamy mixture at 65 degrees F. One mg of 10% BHT is dissolved in 10 ml of ETOH liquid and added to the above mixture and stirred again. Two grams of Vitamin E acetate USP are added and scraped down from the sides of the beaker. In a separate beaker, a lecithin soy solution is made up of 45.45 grams of lecithin soy granules which are dispersed with 0.3 grams of sorbic acid powder and mixed into approximately 53.182 ml of isopropyl palmitate liquid. Twenty two ml of this isopropyl palmitate solution is added to the testosterone mixture, forming a yellow creamy liquid. One gram of L-arginine monochloride dissolved in 1 ml of paraben water, is added and stirred with a hand blender (100 ml of paraben water consists of 1.96 grams NF methyl paraben, 0.96 grams NF propyl paraben, to 3500 ml boiling purified water and heated to 60 degrees C. until the two powders are dissolved and then cooled to 65 degrees F.). Next, 0.3 ml of Polysorbate 80 liquid is slowly added and mixed with a stirring rod as air is incorporated, emulsifying the mixture. 1 ml of propylene glycol is then added to the suspension.

One hundred ml of a cooled Pluronic F 127 gel 20% is prepared by adding 13 grams of the poloxamer (PPO/PEO block copolymer, mw ~12,600) to 0.3 grams potassium sorbate powder plus 100 ml of purified paraben water. The mixture is allowed to cool in the refrigerator until all of the granules have been wetted. Dissolution will take place upon cooling. The Pluronic F 127 gel is then added to the above-formed suspension to form a MPLO containing appropriate amounts of the active ingredients. The mixture is slightly granular at this point.

The mixture is then put through an ointment mill (such as the Exakt Three Roller Grinding Mill, model 50 which can be obtained from Exakt Apparatebau GMBH, Robert-Koch-Str. 5, 22851 Norderstedt) at a 1–2 setting. The temperature is preferably 22 degrees centigrade, and the humidity 52%. The mixture is poured into the mill and scraped into a beaker as it flows from the landing pad of the ointment mill. The mixture is run through the mill three times, or until it becomes smooth and non-granular (i.e. no granules visually or tactily detected). The ointment mill should be rinsed with 70% alcohol for cleaning.

The mixing process, and milling process forms compressed micelles containing testosterone USP granules, which provide a smooth and cosmetically elegant transdermal preparation, that takes advantage of the ability of PLO micelles under pressure to increase the amount of lipophilic compound (testosterone) they can carry percutaneously. The use of an ointment mill through which the MPLO is run two or three times creates a very efficient absorption and a cosmetically elegant transdermal agent.

After running the mixture through the ointment mill twice or thrice, 30 grams of the mixture can be put into a jar, or a syringe disperser which delivers exactly 0.5 grams at a time.

EXAMPLE 2

Effects of a MPLO Hydrogel Preparation (2 Contiguous Studies)

A topical testosterone creme formulation (TC) containing 10% w/w testosterone was prepared in accordance with the procedure of Example 1. The final product contained 100 mg of micronized soy based testosterone (USP) suspended in each gram of a 20% modified pluronic lecithin hydrogel (MPLO) forming a thick creamy product.

Administration Schedule and laboratory assays were as follows. Fifty seven (n 57) men who were self randomized and selected by below normal blood testosterone level were instructed to apply TC cream transdermally by rubbing it into designated skin areas about 4–6" in diameter (palm size) each day at 8 AM and/or 8 PM. The men were further instructed to alternate between scrotal and non-scrotal hairless skin areas where absorption has been shown by Weksler et al. to be the most effective on the back, thigh, upper arm, or abdomen. (Weksler ME, Hormone replacement for men. BMJ 1996 April 6; 312(7035):859–60; Testoderm TTS, Testoderm, and Testoderm with adhesive package inserts. Mountain View, Calif. Alza Pharmaceuticals, 1998; Evans et al., Semin Oncol. 1998;2(suppl 6):112–122, Kopicko et al., Int J STD AIDS. 1999;10:817–820) (see Table 1).

The initial quantity of cream used, measured using a plastic spoon supplied to the subjects, was either ⅛ or ¼ of a level teaspoon (50 mg or 100 mg) applied daily to the aforementioned areas.

Blood was sampled at baseline and at 12 hours after the last application of TC for a baseline and steady state level on a monthly basis. Out of the original 57 men only 22 completed the entire study period of 3 years-6 men used a daily dose of 100 mg of TC, 9 men used 200 mg and 10 men used 50 mg each day. Serum concentrations of free and total testosterone were determined. Blood was tested to determine total T, free T, Dihydrotestosterone (DHT), dehydropepiandrosterone (DHEA), Estradiol (E2), LH and prostate specific antigen or PSA (see Table 1).

The men were seen at 1, 3, 6, 12, 24 and 36 month intervals and asked about their frequency of morning erections (AM erections) and sexual functioning (firmness of erection) at each visit. Twenty two of the original fifty seven study participants completed the entire three year study and these men continue to be monitored regularly (every 3–6 months). A second study comparing paired samples of serum and saliva testosterone evaluated twenty two of the men in whom saliva levels for T, DHT, DHEA circulating hormones as well as Estradiol (E2), Estrone (E1) and Progesterone (P) were measured. Total and free serum testosterone were determined initially and on follow up in all the men in the study.

Data Analysis

Serum testosterone, free testosterone, DHT, luteinizing hormone (LH), DHEA, DHEA-S, estradiol (E2) and prostate specific antigen (PSA) were independently measured by radioimmunoassay at Smith Kline Laboratories (Tarzana, Calif.) and Nicholas Lab (Van Nuys, Calif.) Free levels of testosterone, estrone (E1), estradiol (E2), dihydrotestosterone (DHT), dehydroepiandrosterone (DHEA) and progesterone (P) were measured in both saliva and blood by DiagnosTech International (Osceola, Mich.) from June to December 2000. An independent statistician performed all the initial data analysis and reported the recorded results. Further statistical evaluation was performed by an additional independent consultant.

Results

Total testosterone levels significantly increased in the serum of all patients who participated in the study (22 men mean age 46.6+/−10.5 yrs). Both free and total T concentration for the patients, as a group, increased from subnormal values prior to treatment to within normal range by the end of the first month of TC transdermal testosterone use and remained within the normal range during the subsequent months of treatment see FIG. 1A and Table 1 below.

TABLE 1

Baseline and post-treatment hormone levels in a treatment group n 22, receiving a topical testosterone formulation containing 10% testosterone in accordance with one embodiment of the present invention.

| Subject | Dose (mg) | Total Testosterone (ng/dL) | | | | | Free Testosterone (ng/dL) | | | | |
|---|---|---|---|---|---|---|---|---|---|---|---|
| | | Baseline | 1 mo. | 3 mo. | 12 mo. | 36 mo. | Baseline | 1 mo. | 3 mo. | 12 mo. | 36 mo. |
| JA | 100 | 457 | 200 | 536 | 830 | NA | NA | 0.54 | 1.24 | 3.3 | NA |
| VC | 200/100 | 339 | 743 | 1227 | 969 | 441 | 7.4 | 19.6 | 28.2 | 3.76 | 1.9 |
| BC | 200 | 336 | 208 | NA | NA | NA | 1.6 | 0.8 | NA | NA | NA |
| SD | 100 | 369 | 1024 | NA | 382 | NA | 1.12 | 2.21 | NA | 1.2 | NA |
| CDS | 100/50 | 349 | 2030 | 1360 | 1441 | 441 | 1.03 | 5.2 | 4.71 | 5.4 | 1.9 |
| AH | 200 | 342 | 873 | NA | 582 | NA | 0.9 | 2.46 | NA | NA | NA |
| CH | 200 | 235 | 1918 | 423 | 2304 | NA | 0.69 | 5.4 | 1.2 | 5.6 | NA |
| RH | 100 | 235 | 349 | NA | 520 | NA | NA | 0.98 | NA | 2.3 | NA |
| WI | 50/100 | 265 | NA | 374 | 800 | 1403 | NA | NA | 5.6 | 3.2 | NA |
| RL | 100 | 448 | 424 | 1143 | NA | NA | 1.9 | 1.1 | 3.7 | NA | NA |
| WMC | 200 | 586 | 755 | 1114 | 559 | NA | 1.1 | 2.0 | 24.4 | 8.8 | NA |
| AK | 50 | 424 | NA | NA | 843 | NA | 1.0 | NA | NA | NA | NA |
| RP | 200 | 244 | NA | NA | 399 | NA | 4.8 | NA | NA | 8.8 | NA |
| SQ | 200 | 248 | NA | 1332 | NA | NA | 1.04 | NA | 5.7 | NA | NA |
| JS | 200 | 276 | 378 | 341 | 542 | NA | 12.0 | 1.7 | NA | NA | NA |
| JSZ | 100/50 | 353 | 1864 | 2721 | 783 | 1116 | 8.2 | 5.2 | 5.2 | 3.1 | 4.26 |
| DH | 100/50 | 150 | 1387 | 90 | 1387 | NA | 5.0 | 5.2 | 2.0 | 5.2 | NA |
| DO | 200/50 | 240 | 904 | 1308 | NA | NA | NA | 3.19 | 41.4 | NA | NA |
| DB | 100 | 250 | 2315 | DROP | DROP | DROP | DROP | DROP | DROP | DROP | DROP |
| RN | 100 | 261 | NA | 951 | NA | NA | NA | NA | NA | NA | NA |
| RW | 100/50 | 380 | 286 | 1067 | 629 | NA | 0.86 | 1.8 | 5.6 | 3.0 | NA |
| PK | 200/100 | 329 | 3264 | 1465 | 1057 | NA | 5.1 | 5.2 | 4.59 | 3.5 | NA |

Figure 4:
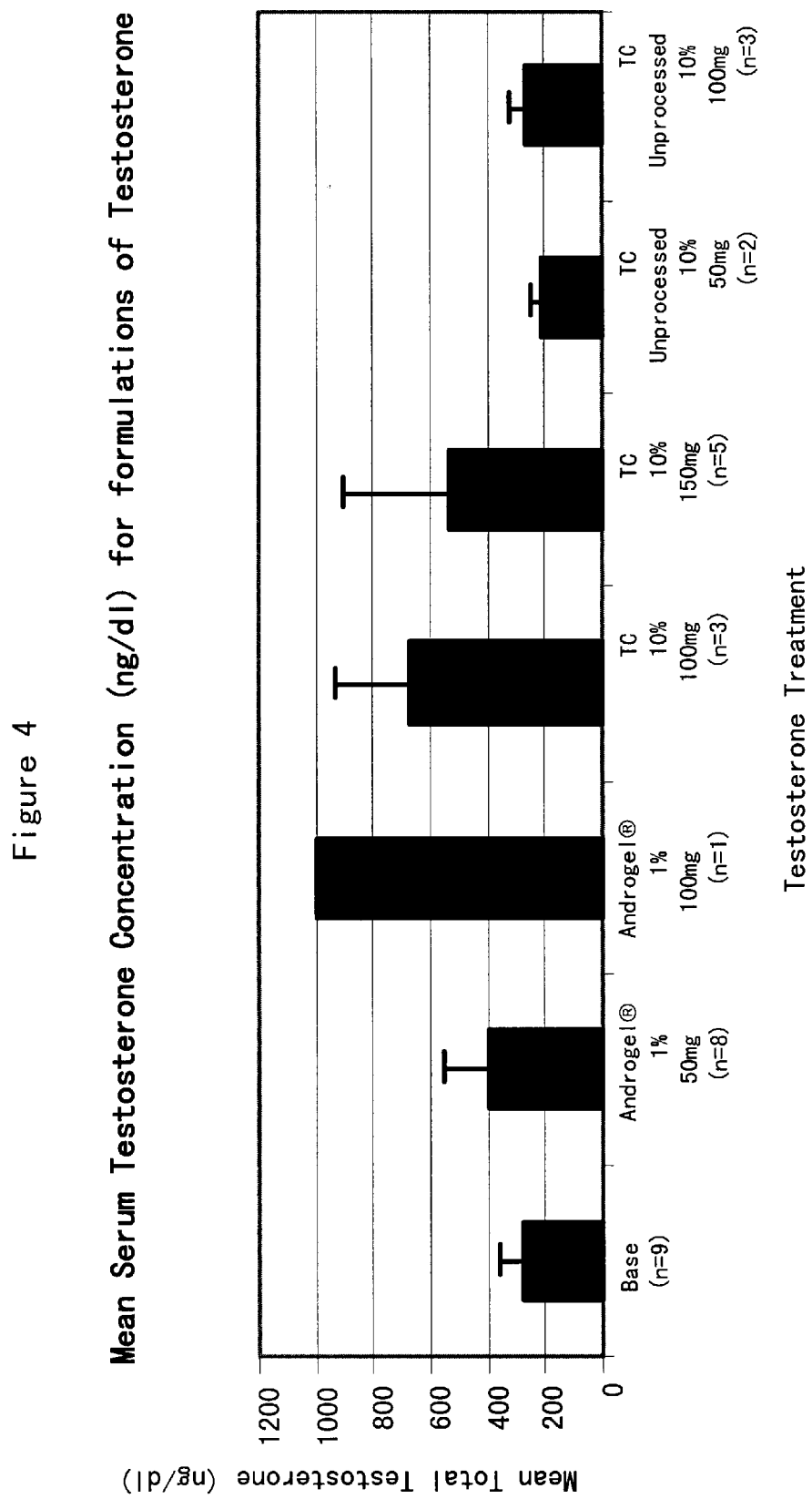
FIG. 4 shows a comparison of the mean levels of total testosterone (350–1,080 ng/dl) measured 14 days after administration of the following doses: 1% Androgel® (50 mg); 10% w/w of present topical formulation (TC) (100 mg); 10% w/w of present topical formulation (TC) (150 mg); 10% w/w unprocessed lotion [blended by homogenizer rather than compressed by ointment mill] (50 mg); 10% w/w unprocessed lotion (100 mg) [blended by homogenizer rather than compressed by ointment mill].

Both libido (AM erections) and sexual functioning (firmness) were evaluated. Libido improved dramatically from pre treatment levels in most of the men. Individual levels of sexual desire, arousal, frequency of sexual activity, orgasm and satisfaction also improved (P<0.001). Over 90% of the men reported an improvement in the symptoms they had experienced prior to treatment with a marked increase in AM erections, penile firmness and libido. DHEA/DHEAS/DHT/FT levels rose with the use of TC but did not change significantly with the use of other topical hormone preparations (FIG. 4).

Prostate-specific antigen (PSA) levels and prostate volume remained in the normal range over the duration of the study (FIG. 2). In all men prostatic examination did not reveal any appreciable changes in size nor was the development of any prostatic cancer stimulated (Ferrando et al., supra). The mean LH concentration and PSA as a group was not significantly different at the end of one year as compared to before treatment. (P>0.001) (FIG. 2).

The testosterone hydrogel was well tolerated, with no application site reactions such as pruritus or irritation noted in any of the men. Cumulative effects did not seem to occur. The transdermal delivery of micronized testosterone in a pharmaceutical base of a modified Pluronic gel, compounded at a 10% concentration was tested in 22 men and found to achieve stable physiologic blood levels (270–1100 pg/dl) of total testosterone within one month of use by these men 22–81 years old.

The results of this study showed that the application of a formula of the invention significantly increased free and total T levels in hypogonadal men. Thus the TC is as effective in raising both total and free T levels as other T delivery methods (the T levels remained stable for up to 36 months in patients using TC, the study shows that the testosterone levels did not accumulate (Table 1).

It is widely thought that serum DHT concentration correlates with prostate enlargement and hair loss, however none of the men in the present study experienced or complained of any of these problems or side effects over the 3 years despite some high DHT levels during treatment. DHT increased from low or normal before treatment to super normal levels at the end of treatment in some men (P<0.001) (data available but not shown). Males with super high DHT levels reported marked increases in sexual drive and arousal frequency (Mantzoros et al., supra, Ellyin et al., abstract, supra). As estrone and estradiol levels remained low with the use of the present formulation, high DHT levels may tend to prevent the conversion of testosterone to estrone or estradiol and thus may improve symptoms of ED related to low libido without risk of prostatic enlargment (Wilson J D., supra; Prehn et al., supra; Gustafsson et al, supra; Mazer, N. Watson Study 2000; Swerdloff et al., supra) (FIGS. 2 and 3).

Although the present study did not statistically analyze the frequency of morning erections or the improvement in sexual functioning, it was observed that the testosterone cream exerted a profound positive effect on both mood and sex drive as self-reported by each of the hypogonadal men (Morley et al., supra). Patients preferred the cream to intramuscular injections in all cases due to the improvement in erections and its ease of use. Evidence from European studies has shown that DHT may also be responsible for increased sexual drive in both men and women (Morley et al., supra).

There were several other benefits noted from transdermal T supplementation. Several men had a normalization of lipid levels which were not statistically evaluated. Results from a study by Swartz et al. suggested that low testosterone levels may be associated with severe coronary artery atherosclerotic disease and myocardial infarction (Swartz et al., supra).

A more recent study reported that testosterone replacement in hypogonadal men may actually have a beneficial effect on lipid metabolism by increasing HDL (Friedl K E et al.Metab 1990 January;39(1):69–74; Zgliczynski et al, supra). They postulate that high blood levels of testosterone might even protect against atherosclerosis especially in men over age 60. Another study by Katherine English suggested that androgens induce coronary vasodilatation and may reduce exercise-induced myocardial ischaemia in patients with angina. (English K M et al., supra).

Prostate exams and monitoring of PSA levels did not show any notable affect on prostatic volume in our study. (FIG. 2). There is ongoing research which points to the fact that the altered testosterone to estrogen ratio may affect the production of PSA glycoprotein if progesterone level (P) is also lowered as well (Yu H., supra). As men age, the proportion of fat to lean tissue gradually increases. Aromatization of testosterone in fat may lead to gradually increased estrogen to testosterone ratios and negative feedback that reduces total testosterone levels. Restoring physiologic levels of progesterone (P) which acts as both an anti-androgen and anti-estrogen may therefore help men prevent prostate cancer by regulating the conversion rate of T to DHT in the prostate.

While it is true that prostate cancers are usually androgen dependent, induction may be related more to estradiol and progesterone levels than testosterone levels (Aver et al., supra). There are minimal progesterone receptors in the stroma of either benign or malignant prostates and progesterone derivatives can act as an inhibitor of 5-alpha-reductase activity in prostate cancer lines (Ellyin et al. abstract, supra). High estrogen or estradiol (E2) in itself may be a promoting factor in prostate cancer (Meacham et al., Urol 14(2):30, 2001; Toxins, supra). However, genetic predisposition or DNA mutation in the epithelial cells of the prostate may ultimately prove to be involved in prostate cancer as the prime initiator (Nankin, H., supra, Knussmann et al., Arch Sex Behav 1986 October;15(5):429–45.). Although the present study was conducted on a short term basis in a limited number of patients, other studies performed by the author evaluating the long term safety risks and benefits, have found transdermal testosterone cream to be both as safe and efficacious as other transdermal systems. (FIG. 4).

In summary the use of a transdermal testosterone based hydrogel or cream provides a simple method of treating hypogonadism which has been shown to be both effective in raising free and total testosterone and more convenient for patients than other existing methods of testosterone delivery. (FIG. 4).

EXAMPLE 3

Pharmacokinetic Behavior of Testosterone in Modified PLO Plus Vitamin E as Measured by Paired Saliva/Serum Using 10% Testosterone in a Modified Pluronic Organogel with Arginine and Alpha Tocopherol The transdermal delivery of micronized testosterone in a pharmaceutical base of modified Pluronic gel, compounded in a 2–10% concentration, was tested in 40 men and found to achieve stable physiologic blood levels (270–1100 ng/dl) of total testosterone within one month of use by men 22–74 years old.

Serial blood and saliva sampling (paired saliva and blood testing results of total and free testosterone, dihydrotestosterone, estradiol and dehydroepiandrosterone (TT, FT, DHT, E2 and DHEA) for pharmacokinetic assessments were performed at pre-dose and intervals ranging from 24 hours to 30 days. During the clinical study, endocrine parameters were measured: Levels of luteinizing hormone (LH) and sex hormone binding globulin (SHBG) were determined over time from Days 14 to Day 28. The determination of salivary Free T, DHT, E2, P, DHEA were performed by Diagnostech International using validated methods (Khan-Dawood et al., Am J Obstet Gynecol February 15, 1984;148(4):441–5). Therapeutic serum free T levels were reached after about 24 hours (FIG. 5) and stabilized within 7–14 days.

Andrological Examinations: An andrological examination was performed at initial screening and follow-up (or at premature discontinuation), and the following were recorded: pubertal rating (axillary hair, pubic hair, penis size), right and left testis (descended, undescended, absent), testicular consistency (soft, firm, hard, not applicable), and seminal vesicle tenderness (tender, non-tender) and prostate examinations: A digital prostate examination was performed at initial screening and the following was recorded: prostate consistency (soft, firm, hard), prostate median groove (present, absent), and prostate tenderness (tender, non-tender).

Vital Signs: Weight and blood pressure were measured at initial screening, baseline (after the wash-out period, if applicable) and follow-up (or at premature discontinuation). Measurements of body fat percentage were performed in some men using the standardized equipment (Skin Fold Calipers) at two body locations. Measurement of body height was performed at initial screening only, and body weight at initial screening, baseline (after the wash-out period, if applicable) and follow-up (or at premature discontinuation). Weight measurements were performed using standardized equipment (a medical office balance scale) and with a minimum of clothing.

PSA (Prostate specific antigen): PSA was measured at initial screening, baseline (after the wash-out period, if applicable) and at Days 180–360 after the initial visit. (FIG. 2).

Serum levels of total testosterone (TT), free and/or bioavailable testosterone (FT or non-SHBG-T), dihydrotestosterone (DHT), and 17-estradiol (E2) were determined in both blood or saliva samples collected prior to the morning dose of trial medication on Day 1, Day 28, Day 60, Day 90, Day 120, Day 150 and Day 180 and in serum/blood samples collected up to 12–24 hours after the previous morning dose. Calculated levels of bioavailable T (non-SHBG-T) represent a reliable index of biologically readily available T. (Vermeulen A, et al., J Clin endocrinol Metab 1999 October;84(10):3666–72.). The following pharmacokinetic parameters were determined to be indicative of the active metabolites of testosterone: DHT/T and E2/T as shown in Table 2 below.

TABLE 2

Baseline and post-treatment hormone levels (12 and 24 hours) in the treatment group (n 8) receiving administration of 10% w/w testosterone formulation in accordance with one embodiment of the present invention.

| Subject | | TT | MC | AK | AC | RH | JS | BR | PR | JG |
|---|---|---|---|---|---|---|---|---|---|---|
| Dose | | 1 gm | 1 gm | 0.5 gm | 0.5 gm | 0.5 gm | 1 gm | 1 gm | 0.5 gm | 0.5 gm |
| Formulation | | Creme | Lotion | Lotion | Lotion | Creme | Creme | Lotion | Creme | Creme |
| Application Situs | | Ribs | Scrotum | Ribs | Ribs | Side | Ribs | Ribs | Ribs | Ribs |
| Time since last dose (hr) | | 20.5 | 25 | 1.5 | 26.6 | 24 | 25 | 48 | 49.5 | 23 |
| | Normal Range | | | | | | | | | |
| Total T (ng/dL) | 350–1080 | 2130 | 233 | 460 | 708 | 415 | 970 | 126 | 2110 | 2160 |
| Free T (pg/mL) | 47–244 | 636.2 | 60.6 | 61.8 | 117.2 | 68.1 | 261.8 | 33.6 | 622.6 | 44.3 |
| SHBG nmol/L) | 3–71 | 17 | 11 | 53 | 43 | 38 | 16 | 9 | 18 | 24 |
| DHT (pg/mL) | 36–573 | 644.1 | 818.7 | 1924 | 804.6 | 1731 | 325 | 341.8 | 1829 | 366 |
| E2 (pg/mL) | 18–73 | 15 | 24 | 31 | 26 | 15 | 27 | 32 | 58 | 24 |
| DHT/T ratio | | 0.030 | 0.351 | 0.418 | 0.114 | 0.417 | 0.034 | 0.271 | 0.087 | 0.160 |
| E2/T ratio | | .0007 | .0103 | .0067 | .0037 | .0036 | .0028 | .0254 | .0027 | .0115 |

There is scientific evidence that low progesterone (P) in saliva may be used to monitor the ovarian cycle (Lu Y C. et al, J Immunoassay May 18, 1997:2 149–63; Finn M M et al., Fertil Steril 1988 December 50:6 882–7). Anecdotally P at very low levels in men may be predictive of prostate cancer and in women low P measurement may signal a potential for breast cancer development (Nomura et al., J Clin Endocrinol Metab 1988 January 66:1230–2; Simpson H W, et al., Eur J Cancer 1995 October 31A:11 1768–72; Fottrell P F, Br J Cancer Suppl 1988 December 9: 98–100). Progesterone also possesses anti-androgen activity in preventing conversion of T to DHT in prostate cells and can decrease aromatase activity (Fortune J E et al., Biol Reprod 1983 June 28:5 1078–89).

EXAMPLE 4

1% Testosterone Cream Use in Women

Although testosterone deficiency is an important disease in males requiring hormone replacement therapy, testosterone is also very useful to restore libido in women. Recently, a user-friendly transdermal cream has been developed. In the present study the pharmacokinetics of this system were assessed in eight healthy female volunteers (n 8).

Method: The study was conducted in 8 healthy females (mean age 54.0, range 45–68) at the Monterey Preventive Medical Clinic in California. After a 12 hour fasting period, a transdermal compounded T cream containing 0.5–1 mg of testosterone in a MPLO base was applied to the inner thighs or the inner arm daily. Plasma concentrations of testosterone and other hormones were measured monthly by radio immunoassay, the results of which are shown in Table 3.

TABLE 3

Baseline and post-treatment hormone levels in serum and saliva in a group of women (n 25) receiving 1% Testosterone applied topically.

| Free Testosterone (pg/mL) | | Total Testosterone (ng/dL) | |
|---|---|---|---|
| Before | After | Before | After |
| 1.5 | 2.2 | 43 | 86.6 |
| 0.3 | 1.4 | 40 | 79 |
| 0.4 | 1.5 | 17.9 | 49 |
| 1.3 | 1.1 | 30 | 70.1 |
| 1 | 10 | 21 | 53 |
| 0.5 | 1.1 | 59 | 111.8 |
| 0.3 | 6.6 | <10 | 22.1 |
| Mean 0.757 | 2.557 | 31.557 | 67.371 |
| S.D. 0.503 | 3.318 | 16.933 | 29.097 |

Figure 6:
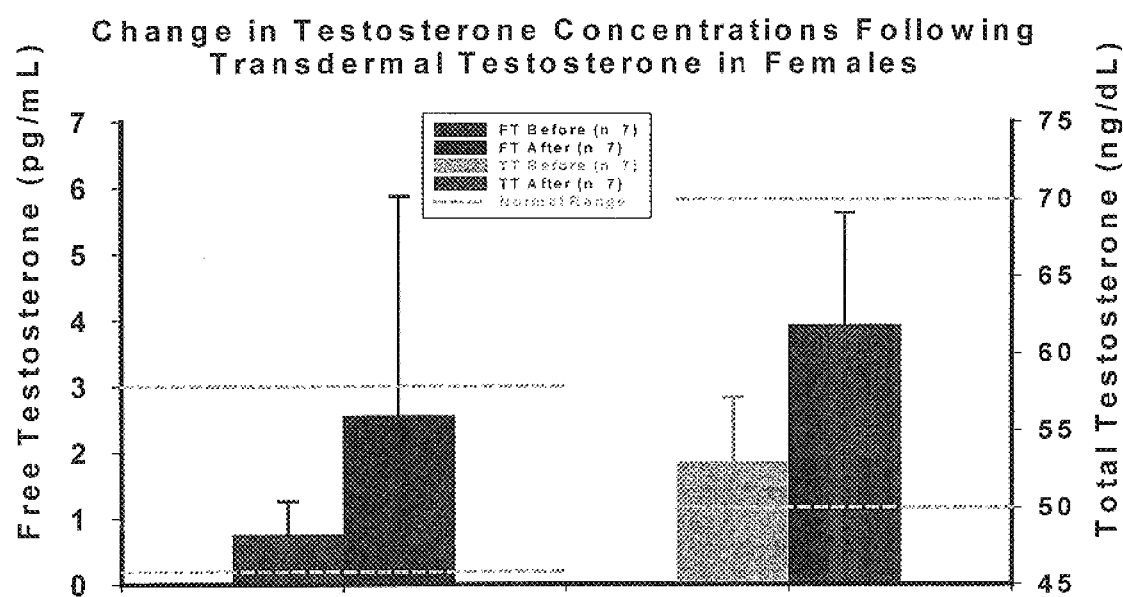
FIG. 6 illustrates free testosterone (FT) and total testosterone (TT) changes in women after receiving testosterone therapy from a topical testosterone formulation made in accordance with one embodiment of the present invention.

Results: The cream was well tolerated by the subjects. Plasma concentrations of testosterone increased after 20–30 days and reached an apparent steady state (median 30±0.5) during the administration period. Total T levels remained in the normal range for females at the dosage range. Most women required between 0.25 to 1.0 mg of T daily in this transdermal form. (FIG. 6).

Conclusions: The transdermal testosterone creme system was well tolerated and showed that administration of testosterone over 12–24 days in healthy female volunteers provided plasma concentrations equal to those within the normal range in females. Therefore, low dose testosterone in a topical cream seems to be appropriate as a form of testosterone replacement therapy in women.

While several particular embodiments of the invention have been illustrated and described, it will be apparent that various modifications can be made without departing from the spirit and scope of the invention. Accordingly, it is not intended that the invention be limited to men only except by the following claims.

What is claimed is:

1. A method of minimizing aromatic conversion of testosterone to an estrogen during testosterone supplementation therapy a patient in need thereof comprising the steps of:
   coadministering to the skin of a subject from a topical formulation, a therapeutically effective amount of testosterone, and an amount of tocopherol that is sufficient to minimize aromatization of the testosterone to an estrogen.

2. The method of claim 1, wherein the topical formulation includes a modified poloxamer lecithin organogel as a carrier.

3. The method of claim 1, further comprising coadministering a therapeutically effective amount of an arginine ingredient from the topical formulation.

4. The method of claim 1, wherein the testosterone is micronized.

5. The method of claim 1, wherein the amount of testosterone is from about 0.5% w/w to about 25% w/w of the topical formulation.

6. The method of claim 5, wherein the amount of testosterone is from about 5% w/w to about 10% w/w of the topical formulation.

7. The method of claim 3, wherein the arginine ingredient is in a salt form.

8. The method of claim 3, wherein the arginine ingredient is L-arginine monochloride.

9. The method of claim 3, wherein the amount of arginine ingredient is from about 5% w/w to about 10% w/w of the topical formulation.

10. The method of claim 1, wherein the tocopherol comprises alpha tocopherol.

11. The method of claim 1, wherein the tocopherol comprises gamma tocopherol.

12. The method of claim 1, wherein the amount of tocopherol is from about 5% w/w to about 10% w/w of the topical formulation.

13. The method of claim 3, further comprising coadministering an effective amount of dehydroepiandrosterone (DHEA) from the topical formulation.

14. The method of claim 1, wherein the DHEA comprises dehydroepiandrosterone sulfate (DHEAS).

15. The method of claim 14, wherein the amount of DHEA is about from about 1% w/w to about 20% w/w of the topical formulation.

16. The method of claims 3, further comprising coadministering an effective amount of melatonin from the topical formulation.

17. The method of claim 16, wherein the amount of melatonin is from about 1% w/w to about 20% w/w of the topical formulation.

18. The method of claim 3, further comprising coadministering an effective amount of progesterone from the topical formulation.

19. The method of claim 18, wherein in the amount of progesterone is from about 1% w/w to about 20% w/w of the topical formulation.

20. The method of claim 3, further comprising coadministering an effective amount of oxytocin from the topical formulation.

21. The method of claim 20, wherein the amount of oxytocin is from about 1% w/w to about 20% w/w of the topical formulation.

22. The method of claim 3, wherein the amount of testosterone is from about 5% w/w to about 10% w/w, the amount of tocopherol is from about 5% w/w to about 10% w/w, and the amount of arginine is from about 5–10% of the topical formulation.

* * * * *